United States Patent [19]
Grobelny

[11] Patent Number: 5,942,504
[45] Date of Patent: *Aug. 24, 1999

[54] AMINE DERIVATIVES OF OXO- AND HYDROXY- SUBSTITUTED HYDROCARBONS

[75] Inventor: Damian Wojciech Grobelny, Victoria, Australia

[73] Assignee: Narhex Limited, Wanchai, The Hong Kong Special Administrative Region of the People's Republic of China

[ * ] Notice: This patent is subject to a terminal disclaimer.

[21] Appl. No.: 08/900,733

[22] Filed: Jul. 25, 1997

Related U.S. Application Data

[62] Division of application No. 08/295,855, filed as application No. PCT/AU93/00103, Mar. 11, 1993, Pat. No. 5,679,688.

[30] Foreign Application Priority Data

Mar. 11, 1992 [AU] Australia .................................. PL1304

[51] Int. Cl.⁶ .......................... C07D 215/48; A61K 31/47
[52] U.S. Cl. .......................... 514/218; 514/247; 514/248; 514/252; 514/253; 514/311; 540/553; 544/237; 544/238; 546/169
[58] Field of Search .................................. 514/218, 247, 514/248, 252, 253, 311; 540/553; 544/237, 238; 546/169

[56] References Cited

U.S. PATENT DOCUMENTS

| | | | |
|---|---|---|---|
| 3,330,857 | 7/1967 | Hess et al. ............................... | 260/471 |
| 5,011,910 | 4/1991 | Marshall et al. ........................ | 530/329 |
| 5,086,165 | 2/1992 | Marshall et al. ........................ | 530/329 |
| 5,093,477 | 3/1992 | Mölling et al. .......................... | 530/328 |
| 5,116,835 | 5/1992 | Rüger et al. ............................. | 514/218 |
| 5,126,326 | 6/1992 | Anderson et al. ........................ | 514/17 |
| 5,132,400 | 7/1992 | Gammill et al. ......................... | 530/317 |
| 5,137,876 | 8/1992 | MacCoss et al. ......................... | 514/23 |
| 5,142,056 | 8/1992 | Kempe et al. ........................... | 546/265 |
| 5,145,951 | 9/1992 | Voges et al. ............................. | 530/330 |
| 5,151,438 | 9/1992 | Sham ....................................... | 514/357 |
| 5,162,538 | 11/1992 | Voges et al. ............................. | 546/336 |
| 5,164,300 | 11/1992 | Marshall et al. ........................ | 435/23 |
| 5,169,952 | 12/1992 | Askin et al. ............................. | 544/137 |
| 5,171,662 | 12/1992 | Sharma ................................... | 435/5 |
| 5,183,826 | 2/1993 | Bills et al. ............................... | 514/411 |
| 5,187,074 | 2/1993 | Treiber et al. ............................ | 435/41 |
| 5,188,950 | 2/1993 | Balani et al. ............................. | 435/120 |
| 5,192,668 | 3/1993 | Treiber et al. ............................ | 435/41 |
| 5,194,605 | 3/1993 | Greenlee et al. ........................ | 540/460 |
| 5,198,426 | 3/1993 | Hamby et al. ............................ | 514/19 |
| 5,212,157 | 5/1993 | Anderson et al. ........................ | 514/17 |
| 5,215,968 | 6/1993 | Nickel et al. ............................. | 514/19 |
| 5,221,665 | 6/1993 | Skiles ....................................... | 514/18 |
| 5,221,667 | 6/1993 | Kaltenbronn et al. ..................... | 514/19 |
| 5,223,633 | 6/1993 | Hoppe et al. ............................. | 556/95 |
| 5,231,153 | 7/1993 | Talley ....................................... | 562/16 |
| 5,235,039 | 8/1993 | Heath, Jr. et al. ........................ | 530/328 |
| 5,235,057 | 8/1993 | Kleemann et al. ....................... | 546/269 |
| 5,248,667 | 9/1993 | Bridge et al. ............................. | 514/15 |
| 5,250,563 | 10/1993 | Chen et al. ............................... | 514/411 |
| 5,254,682 | 10/1993 | Dhanoa et al. ........................... | 540/451 |
| 5,256,677 | 10/1993 | Sham et al. ............................... | 514/351 |
| 5,294,720 | 3/1994 | Jadhav at al. ............................. | 546/265 |
| 5,294,737 | 3/1994 | Ojima ....................................... | 562/444 |
| 5,296,604 | 3/1994 | Hanko et al. ............................. | 546/169 |
| 5,679,688 | 10/1997 | Grobelny ................................. | 514/311 |

FOREIGN PATENT DOCUMENTS

| | | |
|---|---|---|
| 18051/88 | 12/1988 | Australia . |
| 35660/89 | 11/1989 | Australia . |
| 35700/89 | 11/1989 | Australia . |
| 40585/89 | 1/1990 | Australia . |
| 48493/90 | 5/1990 | Australia . |
| 40192/89 | 6/1990 | Australia . |
| 45665/98 | 6/1990 | Australia . |
| 46115/89 | 6/1990 | Australia . |
| 42308/89 | 8/1990 | Australia . |
| 50582/90 | 9/1990 | Australia . |
| 53716/90 | 11/1990 | Australia . |
| 54071/90 | 11/1990 | Australia . |
| 56289/90 | 12/1990 | Australia . |
| 60663/90 | 2/1991 | Australia . |
| 62084/90 | 3/1991 | Australia . |
| 63221/90 | 4/1991 | Australia . |
| 66334/90 | 5/1991 | Australia . |
| 66742/90 | 5/1991 | Australia . |
| 67877/90 | 6/1991 | Australia . |
| 68229/90 | 6/1991 | Australia . |
| 69755/91 | 6/1991 | Australia . |

(List continued on next page.)

OTHER PUBLICATIONS

*Chimica Oggi*, May 1991, Tomasselli et al., "The complexities of AIDS: An assessment of the HIV protease as a therapeutic target", pp. 6–27.

*Journal of Medicinal Chemistry*, vol. 34, No. 8, Aug. 1991, Huff J. R., "HIV Protease: A novel chemotherapeutic target for AIDS", pp. 2305–2314.

Yarchoan et al., Treatment of HIV infection and AIDS, Cecil Textbook of Medicine, 20th Edition, vol. 2, pp. 1880–1888, 1996.

Benditt, AIDS the unanswered questions, Science, vol. 260, pp. 1253–1255, May 1993.

Hemmi et al., Chem. Abstract 112:669, 1990.

Dutta et al., Chem. Abstract 89:197970, 1978.

*Primary Examiner*—Mukund J. Shah
*Assistant Examiner*—Deepak R. Rao
*Attorney, Agent, or Firm*—Morgan & Finnegan, L.L.P.

[57] ABSTRACT

The present invention discloses the compounds of general formula (1)

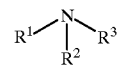

wherein $R^1$, $R^2$, $R^3$ are optionally substituted carbonyl and amide derivatives which are useful as inhibitors of retroviral proteases, and are effective in treating conditions characterized by unwanted activity of these enzymes, such as acquired immune deficiency syndrome.

21 Claims, No Drawings

FOREIGN PATENT DOCUMENTS

| | | |
|---|---|---|
| 71319/91 | 8/1991 | Australia . |
| 71323/91 | 8/1991 | Australia . |
| 71320/91 | 9/1991 | Australia . |
| 74679/91 | 9/1991 | Australia . |
| 77326/91 | 12/1991 | Australia . |
| 78329/91 | 12/1991 | Australia . |
| 82054/91 | 12/1991 | Australia . |
| 78469/91 | 1/1992 | Australia . |
| 81910/91 | 1/1992 | Australia . |
| 82313/91 | 1/1992 | Australia . |
| 82334/91 | 1/1992 | Australia . |
| 83206/91 | 1/1992 | Australia . |
| 83740/91 | 3/1992 | Australia . |
| 87409/91 | 3/1992 | Australia . |
| 85877/91 | 4/1992 | Australia . |
| 87594/91 | 4/1992 | Australia . |
| 87309/91 | 5/1992 | Australia . |
| 87715/91 | 5/1992 | Australia . |
| 88086/91 | 5/1992 | Australia . |
| 90531/91 | 5/1992 | Australia . |
| 90851/91 | 5/1992 | Australia . |
| 90925/91 | 5/1992 | Australia . |
| 91251/91 | 5/1992 | Australia . |
| 91332/91 | 5/1992 | Australia . |
| 88900/91 | 6/1992 | Australia . |
| 89741/91 | 6/1992 | Australia . |
| 91223/91 | 6/1992 | Australia . |
| 89941/91 | 7/1992 | Australia . |
| 91790/91 | 7/1992 | Australia . |
| 10812/92 | 8/1992 | Australia . |
| 15310/92 | 9/1992 | Australia . |
| 17487/92 | 10/1992 | Australia . |
| 16007/92 | 11/1992 | Australia . |
| 18355/92 | 12/1992 | Australia . |
| 19373/92 | 1/1993 | Australia . |
| 19543/92 | 1/1993 | Australia . |
| 21944/92 | 1/1993 | Australia . |
| 24129/92 | 2/1993 | Australia . |
| 24251/92 | 2/1993 | Australia . |
| 22889/92 | 3/1993 | Australia . |
| 24690/92 | 3/1993 | Australia . |
| 26424/92 | 3/1993 | Australia . |
| 27253/92 | 4/1993 | Australia . |
| 28199/92 | 5/1993 | Australia . |
| 31628/93 | 6/1993 | Australia . |
| 34972/93 | 9/1993 | Australia . |
| 35165/93 | 9/1993 | Australia . |
| 38808/93 | 9/1993 | Australia . |
| 35621/93 | 10/1993 | Australia . |
| 37160/93 | 11/1993 | Australia . |
| 41230/93 | 12/1993 | Australia . |
| 41354/93 | 12/1993 | Australia . |
| 41659/93 | 1/1994 | Australia . |
| 44930/93 | 3/1994 | Australia . |
| 49072/93 | 5/1994 | Australia . |
| A 62070/94 | 11/1994 | Australia . |
| 2005340 | 6/1990 | Canada . |
| 2071744 | 12/1992 | Canada . |
| 2075547 | 2/1993 | Canada . |
| 2077002 | 3/1993 | Canada . |
| 2112047 | 6/1994 | Canada . |
| A2 0337714 | 10/1989 | European Pat. Off. . |
| A2 0346847 | 12/1989 | European Pat. Off. . |
| A2 0357332 | 3/1990 | European Pat. Off. . |
| A2 0387231 | 9/1990 | European Pat. Off. . |
| A1 0432974 | 6/1991 | European Pat. Off. . |
| A1 0432975 | 6/1991 | European Pat. Off. . |
| A2 0432695 | 6/1991 | European Pat. Off. . |
| A2 0438311 | 7/1991 | European Pat. Off. . |
| A2 0480714 | 4/1992 | European Pat. Off. . |
| A1 0487270 | 5/1992 | European Pat. Off. . |
| A1 0491538 | 6/1992 | European Pat. Off. . |
| A2 0518675 | 12/1992 | European Pat. Off. . |
| A1 0521686 | 1/1993 | European Pat. Off. . |
| A1 0528661 | 2/1993 | European Pat. Off. . |
| A1 0534511 | 3/1993 | European Pat. Off. . |
| A1 0550924 | 7/1993 | European Pat. Off. . |
| A1 0553357 | 8/1993 | European Pat. Off. . |
| A2 0566237 | 10/1993 | European Pat. Off. . |
| A1 0574135 | 12/1993 | European Pat. Off. . |
| A1 0602306 | 6/1994 | European Pat. Off. . |
| A1 0604183 | 6/1994 | European Pat. Off. . |
| A1 0604184 | 6/1994 | European Pat. Off. . |
| A1 0604185 | 6/1994 | European Pat. Off. . |
| A1 0604186 | 6/1994 | European Pat. Off. . |
| A2 0604182 | 6/1994 | European Pat. Off. . |
| WO 09191/90 | 2/1989 | WIPO . |
| WO 08221/91 | 6/1991 | WIPO . |
| WO 10442/91 | 7/1991 | WIPO . |
| WO 19000/91 | 12/1991 | WIPO . |
| WO 06992/92 | 4/1992 | WIPO . |
| WO 08701/92 | 5/1992 | WIPO . |
| WO 15319/92 | 9/1992 | WIPO . |
| WO 21696/92 | 12/1992 | WIPO . |

AMINE DERIVATIVES OF OXO- AND HYDROXY- SUBSTITUTED HYDROCARBONS

This is a divisional of application Ser. No. 08/295,855 filed Nov. 4, 1994, now U.S. Pat. No. 5,679,688 which is a 371 of PCT/AU93/00103 filed on Mar. 11, 1993.

TECHNICAL FIELD

The invention relates to certain amine derivatives and their use in the inhibition of human immunodeficiency virus (HIV) proteases and thus in the treatment of HIV viral infections such as acquired immunodeficiency syndrome (AIDS).

BACKGROUND ART

Human immunodeficiency virus (HIV) is a pathogenic retrovirus causing AIDS and its related disorders. The development of antiviral chemotherapy against AIDS has been the subject of an intense research effort since the discovery of HIV. (For a recent review on molecular targets for AIDS therapy see Mitsua et al, Science, 1990, pp 1533–1544). The HIV Proteases (HIV PR), and aspartyl proteases, were first suggested as a potential target for AIDS therapy by Kramer et al. (*Science*, 231, 1580, 1986). Since that time the potential usefulness of HIV PR inhibitors as effective agents in treatment of AIDS has been widely recognized (for a review of the HIV PR as a therapeutic target see Tomaselli et al. *Chimica Oggi*, May 1991, pp 6–27 and Huff J. R., *J.Med.Chem.*, 1991, 34, 2314–2327). Of the classical transition state mimics for aspartyl proteases, the hydroxyethylene, dihydroxyethylene, hydroxyethylamine and phosphinic acid isosteres appear to provide the greatest affinity for HIV PR. Many inhibitors of HIV PR have been shown to have an antiviral activity at concentrations in the nanomolar range in the different cell systems and are described as such in the patent literature.

SUMMARY OF THE INVENTION

The invention provides a new class of compounds which are useful as inhibitors of retroviral proteases, particularly aspartyl proteases and more particularly HIV proteases, and which are effective in treating conditions characterized by unwanted activity of these enzymes, in particular acquired immune deficiency syndrome.

A first embodiment of the invention is directed to compounds of the general formula (I):

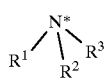

(I)

or pharmaceutically acceptable salts thereof, wherein:

$R^1$ is a group R, wherein R is selected from the group consisting of hydrogen, —R'H, —R'C(O)OR'', —R'C(O)NH$_2$, —R'C(O)NHR'', —R'C(O)NR''R''', —R'NHC(O)R'', —R'NR'''C(O)R'' or —R'C(O)R'', where R'' and R''' are independently optionally substituted (C$_1$–C$_{18}$)alkyl, typically (C$_1$–C$_{12}$)alkyl; (C$_3$–C$_{18}$)cycloalkyl, typically (C$_3$–C$_{12}$) cycloalkyl; (C$_3$–C$_{18}$)cycloalkyl(C$_1$–C$_{18}$)alkyl, typically (C$_3$–C$_{12}$)cycloalkyl(C$_1$–C$_6$)-alkyl; (C$_6$–C$_{24}$)aryl, typically (C$_6$–C$_{16}$)aryl; (C$_7$–C$_{25}$)aralkyl, typically (C$_7$–C$_{16}$)aralkyl; (C$_2$–C$_{18}$)alkenyl, typically (C$_2$–C$_{12}$)alkenyl; (C$_8$–C$_{26}$) aralkenyl, typically (C$_8$–C$_{16}$)aralkenyl; (C$_2$–C$_{18}$)alkynyl, typically (C$_2$–C$_{12}$)alkynyl; (C$_8$–C$_{26}$)aralkynyl, typically (C$_8$–C$_{16}$)-aralkynyl; or heterocyclic, and where R' is an optionally substituted divalent radical derived from (C$_1$–C$_{18}$)alkyl, typically (C$_1$–C$_{12}$)alkyl; (C$_3$–C$_{18}$) cycloalkyl, typically (C$_3$–C$_{12}$)cycloalkyl; (C$_3$–C$_{18}$)-cycloalkyl(C$_1$–C$_{18}$)alkyl, typically (C$_3$–C$_{12}$)cycloalkyl (C$_1$–C$_6$)alkyl; (C$_6$–C$_{24}$)aryl, typically (C$_6$–C$_{16}$)aryl; (C$_7$–C$_{25}$)aralkyl, typically (C$_7$–C$_{16}$)aralkyl; (C$_2$–C$_{18}$) alkenyl, typically (C$_2$–C$_{12}$)alkenyl; (C$_8$–C$_{26}$)aralkenyl, typically (C$_8$–C$_{16}$)aralkenyl; (C$_2$–C$_{18}$)alkynyl, typically (C$_2$–C$_{12}$)alkynyl; (C$_8$–C$_{26}$)aralkynyl, typically (C$_8$–C$_{16}$)-aralkynyl; or heterocyclic, or $R^1$ is

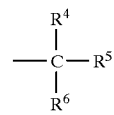

where $R^4$, $R^5$ and $R^6$ are independently a group R as defined above, or $R^4$ has the meaning of R as defined above and $R^5$ and $R^6$ taken together are =O, =S, =NH or =NR; and $R^2$ is

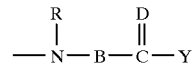

where R is as previously defined; D is O or S; Y is hydrogen, —R or —OR, where R is as previously defined, or is an amino acid, aza-amino acid or peptide residue in which any functional group present is optionally protected; and B is optionally absent or is (C$_1$–C$_6$)-alkylidene, wherein any one or more —CH$_2$— groups may be replaced by —NR—, —NH—, —O— or —S— provided that the compound of Formula (I) does not contain a chain of three or more atoms which are not carbon, and wherein any H atom may be substituted by a group R as previously defined; and optionally N*, N, $R^1$ and R taken together form a cyclic diazaalkane of the formula:

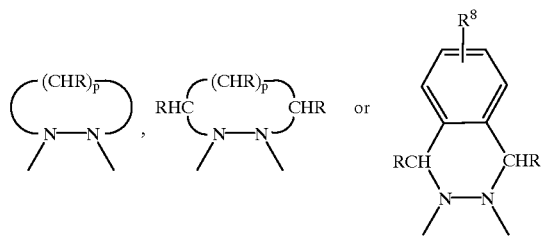

where p is 1 to 3, each R is independently as defined above and $R^8$ is R, —NH$_2$, —NHR, —NR$_2$, —COOH, —COOL, —CHO, —C(O)R, —CN, halo, —CF$_3$, —OL, —SR, —S(O)R, —S(O)$_2$R, —CONH$_2$, —CONHR, —CONR$_2$, —NHOH, —NHOL, —NO$_2$, =O, =S or —NHNH$_2$, wherein each R is independently as defined above and each L is independently R or a hydroxyl protecting group which is labile in vivo; or $R^2$, N* and $R^4$ together form a saturated or unsaturated cyclic, bicyclic or fused ring system as defined hereinafter which may be additionally substituted by —C(O)Y, where Y is as previously defined and $R^3$ is X—W—A'—Q—A—, wherein:

A' and A independently are absent or (C$_1$–C$_8$)alkylidene, typically (C$_1$–C$_4$)alkylidene which may be substituted with one or more substituents R as previously defined; Q is

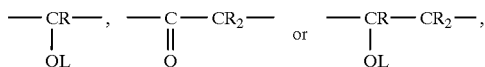

where L and each R, independently of the others, are as previously defined, and optionally Q and A together, or Q and A' together, or A', Q and A together form part of a saturated or unsaturated cyclic, bicyclic or fused ring system as defined hereinafter; W is absent or is N(R), O or S, wherein R is as previously defined; and X is hydrogen, or $X^1$, where $X^1$ is Ra— or RbC(O)— or RbS(O)$_z$—, where z is 1 or 2 and Ra and Rb are independently $(C_1$–$C_{18})$alkyl, typically $(C_1$–$C_{12})$alkyl; $(C_3$–$C_{18})$cycloalkyl, typically $(C_3$–$C_{12})$cycloalkyl; $(C_3$–$C_{18})$cycloalkyl$(C_1$–$C_{18})$alkyl, typically $(C_3$–$C_{12})$cycloalkyl-$(C_1$–$C_6)$alkyl; heterocyclic; $(C_1$–$C_{18})$alkylheterocyclic, typically $(C_1$–$C_{12})$ alkylheterocyclic; heterocyclic$(C_6$–$C_{24})$aryloxy, typically heterocyclic$(C_6$–$C_{16})$aryloxy; $(C_1$–$C_{18})$alkoxy, typically $(C_1$–$C_{12})$-alkoxy; $(C_1$–$C_{18})$alkoxy$(C_1$–$C_{18})$alkyl, typically $(C_1$–$C_{12})$alkoxy-$(C_1$–$C_{12})$alkyl; $(C_6$–$C_{24})$aryloxy$(C_1$–$C_{18})$ alkyl, typically $(C_6$–$C_{16})$-aryloxy$(C_1$–$C_{12})$alkyl; $(C_6$–$C_{24})$ aryloxy$(C_1$–$C_{18})$alkoxy, typically $(C_6$–$C_{16})$aryloxy$(C_1$–$C_{12})$ alkoxy; $(C_6$–$C_{24})$aryl, typically $(C_6$–$C_{16})$aryl; $(C_6$–$C_{24})$aryl $(C_1$–$C_{18})$alkyl, typically $(C_6$–$C_{16})$aryl$(C_1$–$C_{12})$alkyl; $(C_6$–$C_{24})$aryl$(C_1$–$C_{18})$alkylheterocyclic, typically $(C_6$–$C_{16})$ aryl-$(C_1$–$C_{12})$alkylheterocyclic; heterocyclicoxy$(C_1$–$C_{18})$ alkyl, typically heterocyclicoxy$(C_1$–$C_{12})$alkyl; $(C_1$–$C_{18})$ alkylamino, typically $(C_1$–$C_{12})$alkylamino; di$(C_1$–$C_{18})$ alkylamino, typically di$(C_1$–$C_{12})$-alkylamino; $(C_6$–$C_{24})$ arylamino, typically $(C_6$–$C_{16})$arylamino; di-$(C_6$–$C_{24})$ arylamino, typically di$(C_6$–$C_1 6)$arylamino; $(C_7$–$C_{25})$ aralkyl-amino, typically $(C_7$–$C_{12})$aralkylamino or di$(C_7$–$C_{25})$aralkylamino, typically di$(C_7$–$C_{12})$aralkylamino; any of which may be optionally substituted as hereinbelow defined or substituted with a group Re, where Re is a group of the formula:

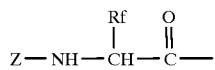

where Z has the meaning of Ra or Rb or is an acylated amino acid, azaamino acid or peptide residue, and Rf is the side-chain of a natural amino acid in which any functional group present is optionally protected;

or X is Re as previously defined, or X is an optionally protected amino acid, azaamino acid or peptide residue; or when W is N(R), then X, N and the substituent R on N together may form a saturated or unsaturated cyclic, bicyclic or fused ring system as defined hereinbelow or N, A' and the substituent R on N together form a saturated or unsaturated cyclic, bicyclic or fused ring system as defined hereinbelow.

Also included within the scope of the invention are compounds wherein two R substituents, not necessarily vicinal, taken together are optionally substituted $(C_2$–$C_{18})$ alkylidene, typically $(C_2$–$C_8)$alkylidene.

Also included within the scope of the invention are compounds wherein the Z—NH bond shown is replaced by a modified isosteric bond, such as CH$_3$—NRa—, RaCH$_2$—NRa—, CH$_3$—CHRa—, HCH=CRa—, RaCH=CRa—, HCOCHRa—, RaCOCHRa—, HCHOHCHRa—, RaCHOHCHRa—, HNRaCO—, HCF=CRa—, RaCF=CRa—, RaS(O)—, RaS(O)$_2$—, RaP(O)ORa—, RaP(O)(ORa)CH$_2$—, RaP(O)(ORa)O—, RaP(O)(ORa)S—, wherein each Ra is independently as previously defined.

As used herein, the term "optionally substituted" means that one or more hydrogen atoms may be replaced by a group or groups selected from: —F, —Cl, —Br, —I, —CF$_3$, —OH, —OR$^{IV}$, —NH$_2$, —NHR$^{IV}$, —NR$^{IV}$R$^V$, —CN, —NO$_2$, —SH, —SR$^{IV}$, —SOR$^{IV}$, —SO$_2$R$^{IV}$, =O, S, =NOH, =NOR$^{IV}$, —NHOH, —NHOR$^{IV}$, —CHO, where R$^{IV}$ and R$^V$ are independently $(C_1$–$C_{18})$alkyl, typically $(C_1$–$C_{12})$alkyl; $(C_3$–$C_{18})$cycloalkyl, typically $(C_3$–$C_{12})$ cycloalkyl; $(C_3$–$C_{15})$-cycloalkyl$(C_1$–$C_{18})$alkyl, typically $(C_3$–$C_{12})$cycloalkyl$(C_1$–$C_6)$alkyl; $(C_6$–$C_{24})$-aryl, typically $(C_6$–$C_{16})$aryl; $(C_7$–$C_{25})$aralkyl, typically $(C_7$–$C_{16})$aralkyl; $(C_2$–$C_{18})$alkenyl, typically $(C_2$–$C_{12})$alkenyl; $(C_8$–$C_{26})$ aralkenyl, typically $(C_8$–$C_{16})$aralkenyl; $(C_2$–$C_{18})$alkynyl, typically $(C_2$–$C_{12})$alkynyl; $(C_8$–$C_{26})$-aralkynyl, typically $(C_8$–$C_{16})$aralkynyl; or heterocyclic.

As used herein, the term "alkyl" includes within its meaning straight and branched chain alkyl groups. Examples of such groups are methyl, ethyl, propyl, isopropyl, butyl, isobutyl, sec-butyl, tert-butyl, amyl, isoamyl, sec-amyl, 1,2-dimethylpropyl, 1,1-dimethylpropyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyloctyl, 1-, 2-, 3-, 4- or 5-ethylheptyl, 1-, 2- or 3-propylhexyl, decyl, 1-, 2-, 3-, 4-, 5-, 6-, 7- or 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5,6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1- or 2-pentylheptyl, and the like.

A used herein, the term "cycloalkyl" refers to mono- or polycyclic alkyl groups, or alkyl substituted cyclic alkyl groups. Examples of such groups include cyclopropyl, methylcyclopropyl, cyclobutyl, methylcyclobutyl, cyclopentyl, methylcyclopentyl, ethylcyclopentyl, cyclohexyl, methylcyclohexyl, ethylcyclohexyl, cycloheptyl, cyclooctyl, cyclononyl, cyclodecyl, cycloundecyl, cyclododecyl, decahydronaphthyl, bicyclo[2.2.1]heptanyl, bicyclo[2.2.2]octanyl and the like.

As used herein, the term "cycloalkylalkyl" refers to an alkyl group substituted with a cycloalkyl group as defined above.

As used herein, the term "alkenyl" includes within its meaning ethylenically mono-, di- or poly-unsaturated alkyl or cycloalkyl groups as previously defined. Examples of such alkenyl groups are vinyl, allyl, 1-methyivinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1,4-pentadienyl, 1,3-cyclopentadienyl, 1,3-headienyl, 1,4-hexadienyl, 1,3-cyclohexadienyl, 1,4-cyclohexadienyl, 1,3 cycloheptadienyl, 1,3,5-cycloheptatrienyl and 1,3,5,7-cyclooctatetraenyl.

As used herein, the term "alkynyl" includes within its meaning acetylenically unsaturated alkyl groups as previously defined. Examples of such alkynyl groups are ethynyl, propynyl, n-butynyl, n-pentynyl, 3-methyl-1-butynyl, n-hexynyl, methyl-pentynyl, $(C_7-C_{12})$alkynyl and $(C_7-C_{12})$ cycloalkynyl.

As used herein, the term "alkylidene" refers to optionally unsaturated divalent alkyl radicals. Examples of such radicals are —$CH_2$—, —$CH_2CH_2$—, —CH=CH—, —$CH_2CH_2CH_2$—, —$C(=CH_2)CH_2$—, —$CH_2CH=CH$—, —$(CH_2)_4$—, —$CH_2CH_2CH=CH$—, —$CH_2CH=CHCH_2$—, and —$(CH_2)_r$— where r is 5–8. The term also refers to such radicals in which one or more of the bonds of the radical from part of a cyclic system. Examples of such radicals are groups of the structure.

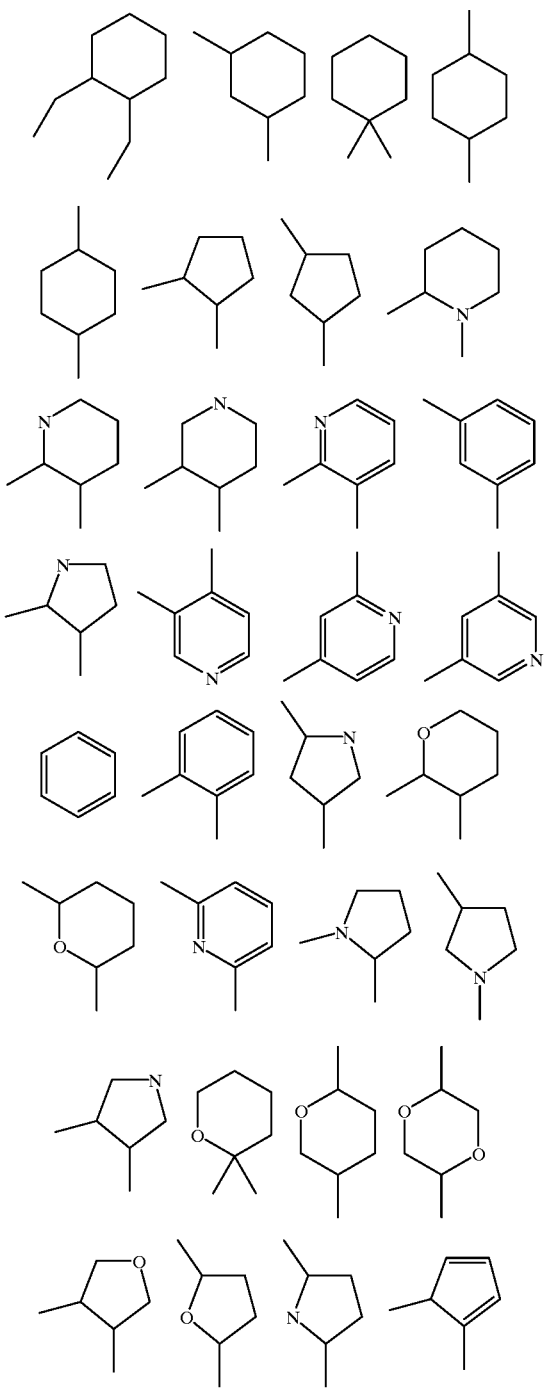

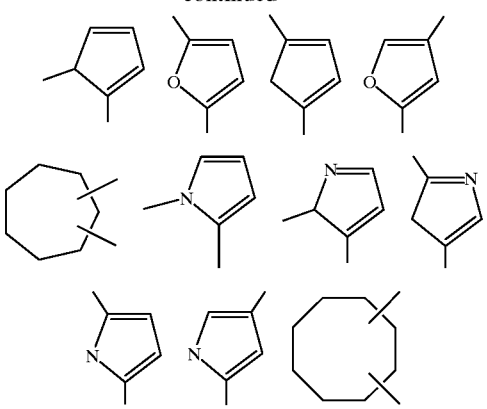

and similar groups wherein any N or O atom is replaced by S.

As used herein, the term "aryl" refers to single, polynuclear, conjugated and fused residues of aromatic hydrocarbons or aromatic heterocyclic ring systems. Examples of such groups are phenyl, biphenyl, terphenyl, quaterphenyl, naphthyl, tetrahydronaphthyl, anthracenyl, dihydroanthracenyl, benzanthracenyl, dibenzanthracenyl, phenanthrenyl, fluorenyl, pyrenyl, indenyl, azulenyl, chrysenyl, pyridyl, 4-phenylpyridyl, 3-phenylpyridyl, thienyl, furyl, pyrryl, indolyl, pyridazinyl, pyrazolyl, pyrazinyl, thiazolyl, pyrimidinyl, quinolinyl, isoquinolinyl, benzofuranyl, benzothienyl, purinyl, quinazolinyl, phenazinyl, acridinyl, benzoxazolyl, benzothiazolyl and the like. In all cases, any available position of the fused or conjugated bicyclic system can be used for attachment to the remainder of the molecule of formula (1).

As used herein, the term "aralkyl" refers to alkyl groups substituted with one or more aryl groups as previously defined. Examples of such groups are benzyl, 2-phenylethyl and 1-phenylethyl.

As used herein, the terms "aralkenyl" and "aralkynyl" refer to alkenyl and alkynyl groups respectively, substituted with one or more aryl groups as previously defined. Examples of such groups are styryl, phenylacetylenyl and 2-phenyl-2-butenyl.

As used herein the term "saturated or unsaturated cyclic, bicyclic or fused ring system" refers to a cyclic system of up to 16 carbon atoms, up to 3 of which may be replaced by O, S or N, which ring system may be substituted with one or more of R, —$NH_2$, —NHR, —$NR_2$, —COOH, —COOL, —CHO, —C(O)R, —CN, halo, —$CF_3$, —OL, —SR, —S(O)R, —$S(O)_2R$, —$CONH_2$, —CONHR, —$CONR_2$, —NHOH, —NHOL, —$NO_2$, =O, =S or —$NHNH_2$; wherein each L and R are independently as previously defined. Examples of such ring systems are those cyclic alkylidene groups exemplified above and

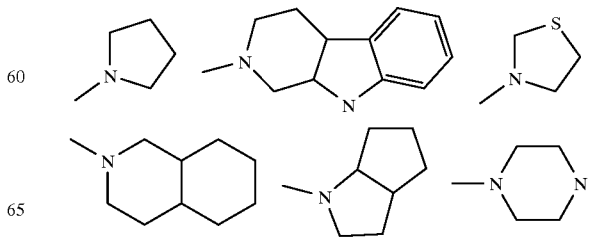

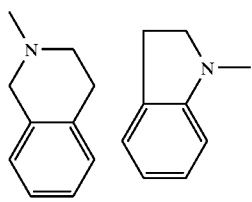

As used herein, the term "heterocyclic" refers to any 3- to 16-membered monocyclic, bicyclic or polycyclic ring containing, for 3- and 4-membered rings, one heteroatom; for 5-membered rings, one or two heteroatoms; for 6- and 7-membered rings, one to three heteroatoms; for 8-and 9-membered rings, from one to four heteroatoms; for 10- and 11-membered rings, from one to five heteroatoms; for 12- and 13-membered rings, from one to six heteroatoms; for 14- and 15-membered rings, from one to seven heteroatoms; and for 16-membered rings, from one to eight heteroatoms; the heteroatom(s) being independently selected from oxygen, nitrogen and sulphur. The term "heterocyclic" includes any group in which a heterocyclic ring is fused to a benzene ring. Examples of heterocyclics are pyrryl, pyrimidinyl, quinolinyl, isoquinolinyl, indolyl, piperidinyl, pyridinyl, furyl, thiophenyl, tetrahydrofuryl, imidazolyl, oxazolyl, thiazolyl, pyrenyl, oxazolidinyl, isoxazolyl, isothiazolyl, isoxazolidinyl, imidazolidinyl, morpholinyl, pyrrolidinyl, pyrazolyl, pyrazolinyl, furfuryl, thienyl, benzothienyl, benzoxazolyl, benzisoxazolyl, benzothiazolyl, benzoisothiazolyl, benzothiadiazolyl, tetrazolyl, triazolyl, thiadiazolyl, benzimidazolyl, pyrrolinyl, quinuclidinyl, azanorbornyl, isoquinuclidinyl and the like. Nitrogen-containing heterocyclics may be substituted at nitrogen with an oxygen atom. Sulfur-containing heterocyclics may be substituted at sulfur with one or two oxygen atoms.

Configurations which result in unstable heterocyclics are not included within the scope of the definition of "heterocyclic" or "saturated or unsaturated cyclic, bicyclic or fused ring system".

As used herein, the term "alkylheterocyclic" refers to a heterocyclic group as defined above, which is substituted with an alkyl group as defined above.

As used herein, the term "heterocyclic-oxy-alkyl" refers to a group of the formula heterocyclic-O-alkyl, wherein the heterocyclic and alkyl are as defined above.

As used herein, the term "alkoxy" refers to a group of the formula alkyl-O—, wherein the alkyl group is as defined above.

As used herein, the term "aryloxy" refers to a group of the formula aryl-O—, wherein the aryl group is as defined above.

As used herein, the term "alkanoyloxy" refers to a group of the formula alkyl-C(O)O—, wherein the alkyl group is as defined above.

As used herein, the term "amino acid" refers to a synthetic or naturally occurring compound of the formula $H_2NCH(R)COOH$, wherein R is as defined above.

As used herein, the term "azaamino acid" refers to an amino acid in which the CH(R) group has been replaced by a group —N(R)—, wherein R is as defined above.

Suitable pharmaceutically acceptable salts of the compound of formula (I) are salts of pharmaceutically acceptable inorganic acids such as hydrochloric, sulphuric, phosphoric, nitric, carbonic, boric, sulfamic, hydrobromic or hydriodic, or with pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic or valeric.

The expression "protected" as used herein is intended to mean that a reactive group such as hydroxyl or amino is substituted by replacing a hydrogen atom of the reactive group in order to protect such groups during synthesis and/or to prevent premature metabolism of the compound of formula (I) after administration to a patient before the compound can reach the desired site of action. Suitable protecting groups for hydroxyl substituents include substituted methyl ethers, for example, methoxymethyl, benzyloxymethyl and the like, vinyl, acyl and carbonate groups. Suitable protecting groups for amino substituents include acyl groups such as acetyl, t-butylacetyl, t-butyloxycarbonyl, benzoyl or carbobenzyloxycarbonyl, benzyloxycarbonyl, pyridinemethoxycarbonyl, quinoline-2-carbonyl or an aminoacyl residue. Protecting groups which are included in the compound of formula (I) must be amenable to hydrolytic or metabolic cleavage in vivo.

Usually, the compound of the general formula (I) will have the structure represented by formula (IA):

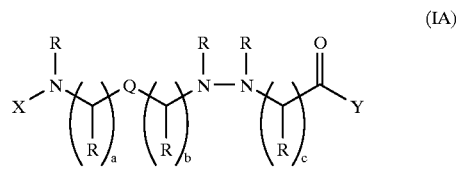

(IA)

where X, Q, Y and each R is independently as previously defined, a and b are independently 0 to 4 and c is 0 to 6, or where two R groups, not necessarily vicinal, taken together are —$(CHR^{18})_m$— where m is 2–8 and $R^{18}$ has the meaning of R.

More usually, the compound of the general formula (I) will have the structure represented by formula (IB):

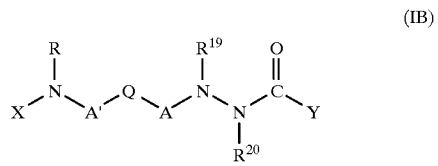

(IB)

where X, R, A', Q, A and Y are as previously defined or either or both of A and A' are absent, and $R^{19}$ and $R^{20}$ have the meaning of R or where $R^{19}$, N*, N and $R^{20}$ together form a cyclic diazaalkane as previously defined.

Most usually, the compound of the general formula (I) will have the structure represented by formula (IC) or (ID):

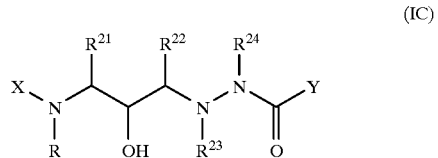

(IC)

-continued

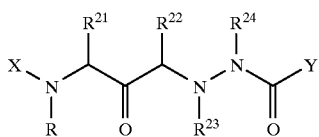
(ID)

wherein:

R is as defined above;

$R^{21}$ is hydrogen, optionally substituted $(C_1-C_{12})$alkyl; optionally substituted $(C_6-C_{12})$aryl; optionally substituted $(C_7-C_{16})$aralkyl;

$R^{22}$ is hydrogen, $(C_1-C_8)$alkyl; $(C_7-C_{16})$aralkyl, or when $R^{21}$ and $R^{22}$ taken together are —$(CH_2)_n$—, wherein n is 2 to 8;

$R^{23}$ is hydrogen; optionally substituted $(C_1-C_{12})$alkyl; $(C_6-C_{12})$aryl; $(C_7-C_{16})$aralkyl; or wherein $R^{22}$ and $R^{23}$ taken together are —$(CHR^{25})_m$—, wherein m is 3–6 and $R^{25}$ has the meaning of $R^{10}$;

$R^{24}$ is hydrogen; optionally substituted $(C_1-C_{12})$alkyl; optionally substituted $(C_7-C_{16})$aralkyl; or optionally substituted $(C_6-C_{12})$aryl;

or wherein $NR^{23}$ and $NR^{24}$ taken together may be a cyclic diazaalkane as previously defined; and X and Y are as previously defined.

Representative compounds in accordance with the invention are:

(i) t-butyl 3-isopropyl-3-[(2R or S,3S)-2-hydroxy-3-(phenylmethoxy-carbonyl)amino-4-phenylbutyl]carbazate, (ii) t-butyl 3-isopropyl-3-[(2R or S,3S)-2-hydroxy-3-(N-quinaldyl-L-valyl)amino-4-phenylbutyl]carbazate, (iii) t-butyl 3-isopropyl-3-[(2R or S,3S)-2-hydroxy-3-(N-quinaldyl-L-asparaginyl)amino-4-phenylbutyl]carbazate, (iv) t-butyl 3-isopropyl-3-[(3S)-2-oxo-3-(N-quinaldyl-L-asparaginyl)amino-4-phenylbutyl]carbazate, (v) t-butyl 3-(1-methyl-3-phenylpropen-3-yl)-3-[(2R or S,3S)-2-hydroxy-3-(phenylmethoxycarbonyl)amino-4-phenylbutyl]carbazate, (vi) t-butyl 3-(1-methyl-3-phenylpropyl)-3-[(2R or S,3S)-2-hydroxy-3-(N-quinaldyl-L-asparaginyl)amino-4-phenylbutyl]carbazate, (vii) cis-1,6-3-t-butoxycarbonyl-4-[(2R or S,3S)-2-hydroxy-3-amino-4-phenylbutyl]-3,4-diazabicyclo[4.4.0]decane, (viii) cis-1,6-3-t-butoxycarbonyl-4-[(2R or S,3S)-2-hydroxy-3-(phenylmethoxycarbonyl)amino-4-phenylbutyl]-diazabicyclo[4.4.0]decane, (ix) cis-1,6-3-t-butoxycarbonyl-4-[(2R or S,3S)-2-hydroxy-3-(N-quinaldyl-L-valyl)amino-4-phenylbutyl]-3,4-diazabicyclo[4.4.0]decane (x) cis-1,6-3-t-butoxycarbonyl-4-[(2R or S,3S)-2-hydroxy-3-[N-(2-pyridyl)methoxycarbonyl)-L-valyl)amino-4-phenylbutyl]-3,4-diaza-bicyclo[4.4.0]decane (xi) cis-1,6-3-t-butoxycarbonyl-4-[(2R or S,3S)-2-hydroxy-3-(N-quinaldyl-L-asparaginyl)amino-4-phenylbutyl]-3,4-diazabicyclo[4.4.0]decane, (xii) cis-1,6-3-t-butoxycarbonyl-4-[(2R or S,3S)-2-hydroxy-3-(N-quinaldyl-L-glutaminyl)amino-4-phenylbutyl]-3,4-diazabicyclo[4.4.0]decane, (xiii) cis-1,6-3-t-butoxycarbonyl-4-[(2R or S,3S)-2-hydroxy-3-(N-quinaldyl-L-threonyl)amino-4-phenylbutyl]-3,4-diazabicyclo[4.4.0]decane, (xiv) 2-t-butoxycarbonyl-3-[(2R or S,3S)-2-hydroxy-3-(phenylmethoxy-carbonyl)amino-4-phenylbutyl]-2,3-diazabicycio[2.2.1]hept-5-ene, (xv) 2-t-butoxycarbonyl-3-[(2R or S,3S)-2-hydroxy-3-(phenylmethoxy-carbonyl)amino-4-phenylbutyl]-2,3-diazabicyclo[2.2.1]heptane, (xvi) 2-t-butoxycarbonyl-3-[(2R or S,3S)-2-hydroxy-3-(N-(2-pyridyl)-methoxy-L-valyl)amino-4-phenylbutyl]-2,3-diaza-bicyclo[2.2.1]heptane, (xvii) 2-[N-(1S)(2-methyl-1-methoxycarbonylpropyl)carbamoyl]-3-[(2R or S,3S)-2-hydroxy-3-[N-(2-pyridyl)methoxy-L-valyl]amino-4-phenylbutyl]-2,3-diazabicyclo [2.2.1]heptane, (xviii) 2-t-butoxycarbonyl-3-[(2R or S,3S)-2-hydroxy-3-(N-quinaldyl-L-asparaginyl)amino-4-phenylbutyl]-2,3-diazabicyclo[2.2.1]heptane, (ixx) 1-[2-(2-pyridyl)methoxycarbonylamino-]benzoyl-2-[(2R or S,3S)-2-hydroxy-3-(N-quinaldyl-L-asparaginyl)amino-4-phenylbutyl]-2-isopropylhydrazine, (xx) 2-t-butoxycarbonyl-3-[(2R or S,3S)-2-hydroxy-3-(N-quinaldyl-L-asparaginyl)amino-4-phenylbutyl]-1,2,3,4-tetrahydrophthalazine, (xxi) 1-trimethylacetyl-2-[(2R or S,3S)-2-hydroxy-3-(phenylmethoxycarbonyl)amino-4-phyenylbutyl]-2-isopropylhydrazine, (xxii) 1-trimethylacetyl-2-[(2R or S,3S)-2-hydroxy-3-(N-quinaldyl-L-asparaginyl) amino-4-phenylbutyl]-2-isopropylhydrazine, (xxiii) 1-(t-butylamino)carbonyl-2-[(2R or S,3S)-2-hydroxy-3-(N-quinaldyl-L-asparaginyl)amino-4-phenylbutyl]-2-isopropylhydrazine, (xxiv) t-butyl 3-isopropyl-3-[(2R or S,3S)-2-hydroxy-3-(N-picolinyl-L-asparaginyl)amino-4-phenylbutyl]carbazate, (xxv) t-butyl 3-isopropyl-3-[(2R or S,3S)-2-hydroxy-3-(N-(2-pyridyl)-methoxycarbonyl-anthranilyl)amino-4-phenylbutyl]carbazate.

(xxvi) t-butyl 3-benzyl-3-[(2R or S,3S)-2-hydroxy-3-(phenylmethoxycarbonyl)amino-4-phenylbutyl]carbazate, (xxvii) t-butyl 3-benzyl-3-[(2R or S,3S)-2-hydroxy-3-(N-quinaldyl-L-asparaginyl)amino-4-phenylbutyl]carbazate, (xxviii) t-butyl 3-cyclohexyl-3-[(2R or S, 3S)-2-hydroxy-3-(phenyl-methoxycarbonyl)amino-4-phenylbutyl]carbazate, (xxix) t-butyl 3-cyclohexyl-3-[(2R or S,3S)-2-hydroxy-3-(N-quinaldyl-L-asparaginyl)amino-4-phenylbutyl]carbazate, (xxx) t-butyl 3-isopropyl-3-[(2R or S,3S)-2-hydroxy-3-(N-(1-carbamoyl-methyl)acryloyl)amino-4-phenylbutyl]carbazate, (xxxi) t-butyl 3-isopropyl-3-[(2R or S,3S)-2-hydroxy-3-(N-(2(RS)-3-tert-butylthio-2-carbamoyl-methylpropionyl)amino-4-phenylbutyl]carbazate, (xxxii) t-butyl 3-isopropyl-3-[(2R or S,3S)-2-hydroxy-3-(N-(1-benzoyl-L-asparaginyl)amino-4-phenylbutyl]carbazate, (xxxiii) 1-t-butyloxycarbonyl-2-[(2R or S,3S)-2-hydroxy-3-(phenylmethoxycarbonyl)amino-4-phenylbutyl]hexahydropyridazine, (xxxiv) 1-t-butyloxycarbonyl-2-[(2R or S,3S)-2-hydroxy-3-(N-quinaldyl-L-asparaginyl)amino-4-phenylbutyl]hexahydropyridazine, (xxxv) cis-1,6-3-t-butoxycarbonyl-4-[(2R or S, 3S)-2-hydroxy-3-(N-quinaldyl-3-cyano-L-alanyl)amino-4-phenylbutyl]-3,4-diaza-bicyclo[4,4,0]decane.

The structures of representative compounds of the invention are as follows:

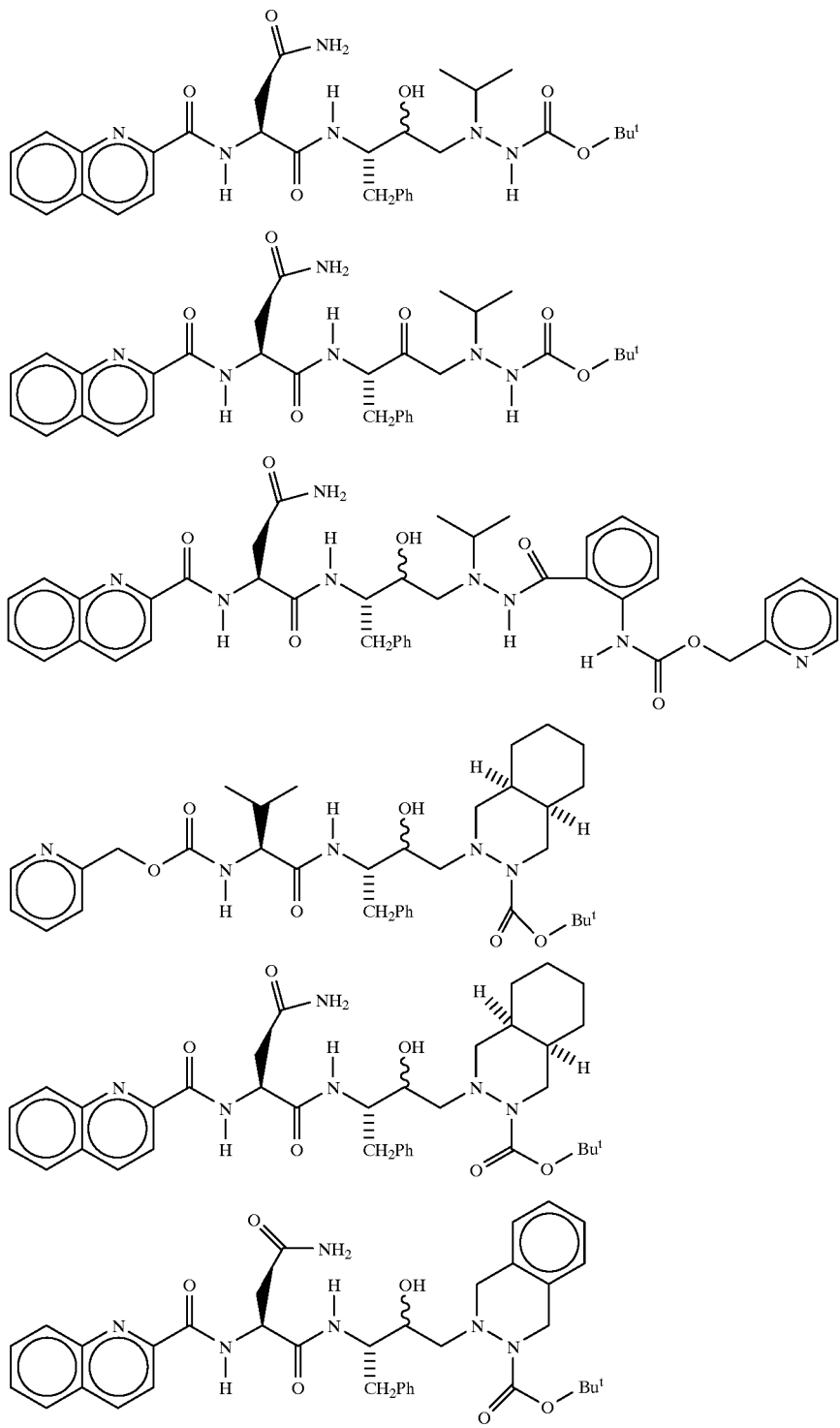
The compound of formula (I), (IA), (IB), (IC) or (ID) can exist in optically isomeric forms and the present invention includes within its scope all these forms in all proportions including all diastereoisomers and racemic mixtures.
The compounds of formula (I) may be prepared by known methods for the synthesis of substituted amines. For example, a compound of the formula
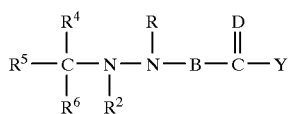

may be prepared by reaction of an amine of the formula

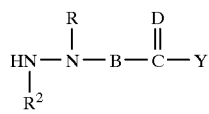

with a substituted alkyl halide of the formula

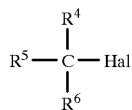

Compounds of formula (IA) may be prepared by reacting an amine of formula

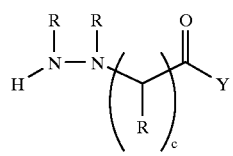

with a halide of formula

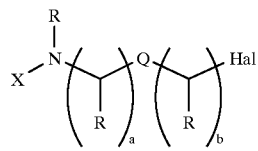

Compounds of formula (IB) may be prepared by reacting an amine of formula

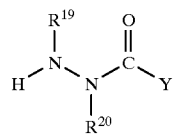

with a halide of formula

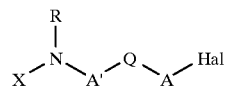

The compounds of formula (IC) can be prepared by reacting a compound of formula (II)

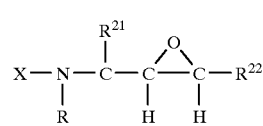

(II)

wherein X, $R^{21}$, $R^{22}$ and R have the significance given earlier, with a compound of formula (III)

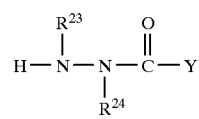

(III)

wherein $R^{23}$, $R^{24}$ and Y have the significance given earlier.

A compound of formula (ID) may be obtained from a compound of formula (IC) by oxidation in accordance with known methods of oxidative transformations of alcohols to ketones.

A compound of formula (ID) may be also be obtained by reacting a compound of formula (IIa)

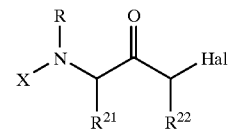

(IIa)

wherein X, R, R21 and R22 are as previously defined and Hal is a group selected from —Cl, —Br, —I or —OS(0)$_2$R, with a compound of formula (III).

The methods of preparation of compounds of formula (IC) and (ID) may be represented by the following general Schemes I to 3. In the Schemes presented herein, the following abbreviations are made:

AA refers to amino acid or amino acid residue; AcCN refers to acetonitrile; BOP refers to benzotriazol-1-yloxytris (dimethylamino)-phosphonium hexafluorophosphate; CBZ refers to carbobenzoxy; CD1 refers to N,N'-carbonyldiimidazole; DMF refers to dimethylformamide; DMSO refers to dimethylsulfoxide; HBT refers to 1-hydroxybenzotriazole; Py refers to pyridine; Py.xSO$_3$ refers to the pyridine complex of sulfur trioxide; RT refers to room temperature and L-Val refers to L-valine.

SCHEME 1

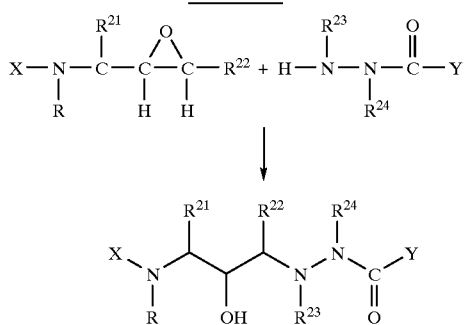

SCHEME 2

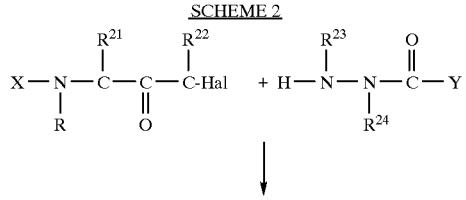

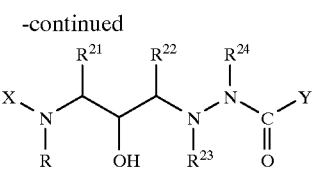

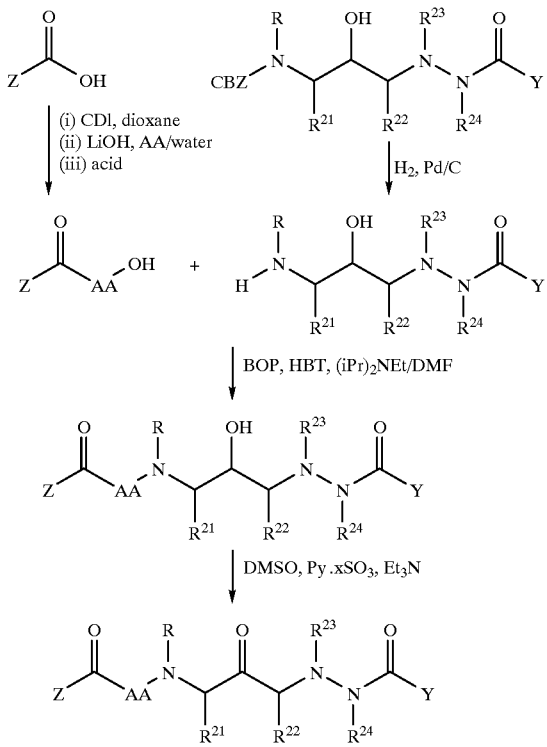

The reaction schemes illustrated can be carried out by generally known methods as exemplified hereinafter. The amino acids or peptide mimics for use in the synthesis of compounds of this invention are generally commercially available or may be prepared by conventional methods of organic chemistry.

Synthetic routes to the intermediates (II), (IIa) and (III) are readily available. The chiral aminoalkylepoxides of formula (II) can be obtained using methods described in the following:

(a) Evans, B. E., et al., J. Org. Chem., 50, 4615–4625 (1985);

(b) Luly, J. R., et al., J. Org. Chem., 52, 1487–1492 (1987);

(c) Handa, B. K., et al., European Patent Application No. 346,847-A2 (1989) and (d) Marshall, G. R., et al., International Patent Application No WO91/08221.

The N-protected aminoalkyl halomethylketones (IIa) are commercially available or can be prepared using methods described in:

(e) Rich, et al., J. Med. Chem., 33, 1285–1288 (1990) and (f) Reference (d) above.

The hydrazide intermediates (III) can be obtained using known methods such as those described in the following:

(g) Dutta, A. S., et al., J. Chem. Soc. Perkin Trans. I, (1975) 1712–1720, (h) Ghali, N. I., et al., J. Org. Chem., 46, 5413–5414 (1981), (i) Gante, J., Synthesis (1989) 405–413 and (j) Houben-Weyl's Methoden der Organische Chemie, vol. 16a, Part 1, pp 421–855; Georg Thieme Verlag, Stuttgart (1990)

A second embodiment of the invention is directed to pharmaceutical compositions comprising a compound of formula (I) together with one or more pharmaceutically acceptable carriers, diluents, adjuvants and/or excipients.

In a third embodiment of the invention there is provided a method for inhibiting retroviral proteases in a mammal in need of such inhibition, comprising administering to the mammal an effective amount of a compound of the first embodiment or of a composition of the second embodiment. In one form of the third embodiment, there is provided a method for the treatment or prophylaxis of HIV viral infections such as AIDS.

For inhibiting retroviral proteases or the treatment of HIV viral infections, a composition of the second embodiment may be administered orally, topically, parenterally, e.g. by injection and by intra-arterial infusion, rectally or by inhalation spray.

For oral administration, the pharmaceutical composition may be in the form of tablets, lozenges, pills, troches, capsules, elixirs, powders, granules, suspensions, emulsions, syrups and tinctures. Slow-release, or delayed-release, forms may also be prepared, for example in the form of coated particles, multi-layer tablets or microgranules.

Solid forms for oral administration may contain pharmaceutically acceptable binders, sweeteners, disintegrating agents, diluents, flavourings, coating agents, preservatives, lubricants and/or time delay agents. Suitable S binders include gum acacia, gelatin, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethylcellulose, polyvinylpyrrolidone, sodium alginate or cetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further comprise one or more emulsifying agents. Suitable emulsifying agents include dispersing agents as exemplified above or natural gums such as gum acacia or gum tragacanth.

For topical administration, the pharmaceutical composition may be in the form of a cream, ointment, gel, jelly, tincture, suspension or emulsion.

The pharmaceutical composition may contain pharmaceutically acceptable binders, diluents, disintegrating agents, preservatives, lubricants, dispersing agents, suspending agents and/or emulsifying agents as exemplified above.

For parenteral administration, the compound of formula I or its salt may be prepared in sterile aqueous or oleaginous solution or suspension. Suitable mono-toxic parenterally acceptable diluents or solvents include water, Ringer's solution, isotonic salt solution, 1,3-butanediol, ethanol, propylene glycol or polyethylene glycols in mixtures with water. Aqueous solutions or suspensions may further comprise one or more buffering agents. Suitable buffering agents include sodium acetate, sodium citrate, sodium borate or sodium tartrate, for example.

For rectal administration, the compound of formula I is suitably administered in the form of an enema or suppository. A suitable suppository may be prepared by mixing the active substance with a non-irritating excipient which is solid at ordinary temperatures but which will melt in the rectum. Suitable such materials are cocoa butter and polyethylene glycols. Suitable enemas may comprise agents as exemplified above with reference to forms for topical administration.

Suitably, an inhalation spray comprising a compound of formula I will be in the form of a solution, suspension or emulsion as exemplified above. The inhalation spray composition may further comprise an inhalable propellant of low toxicity. Suitable propellants include carbon dioxide or nitrous oxide.

The dosage form of the compound of formula I will comprise from 0.01% to 99% by weight of the active substance. Usually, dosage forms according to the invention will comprise from 0.1% to about 10% by weight of the active substance.

The compound of formula I may be administered together or sequentially with 1 or more other active substances known or believed to be effective for the treatment of HIV viral infections. Examples of such other active substances include AZT and acyclovir.

BEST MODE OF CARRYING OUT THE INVENTION

Methods for the preparation of compounds of formula (IC) are described in the following Schemes 1a and 2a:

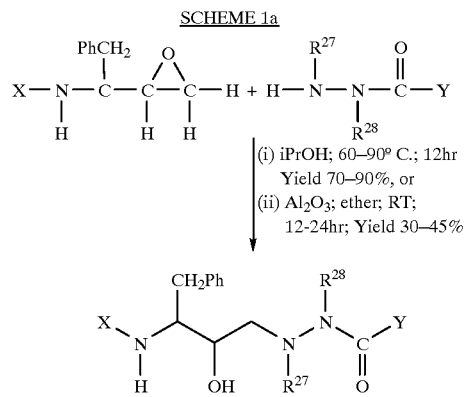

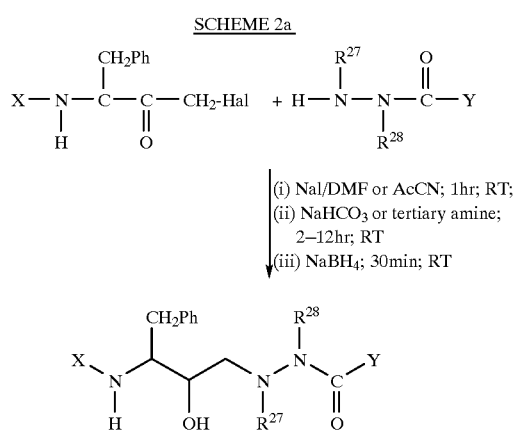

Scheme 3a presents an alternative method of preparation of compounds of formula (IC) and (ID):

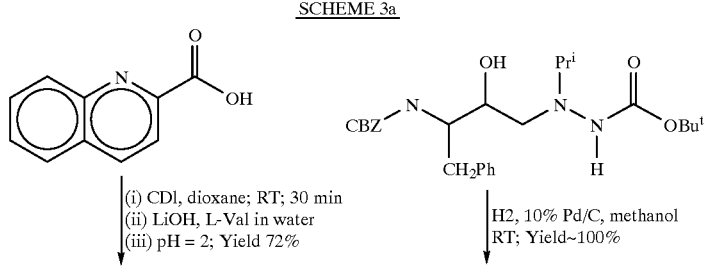

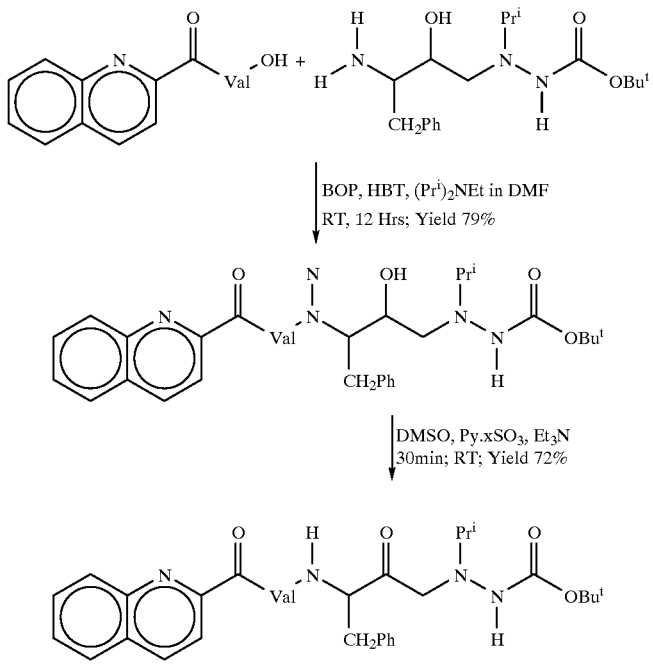

Compositions of the second embodiment may be prepared by means known in the art for the preparation of pharmaceutical compositions including blending, grinding, homogenising, suspending, dissolving, emulsifying, dispersing and mixing of the compound of formula (I) together with the selected excipient(s), carrier(s), adjuvant(s) and/or diluent(s).

In the method for the treatment of HIV viral infections in accordance with the third embodiment of the invention, a compound of the first embodiment will usually be administered orally or by injection. A suitable treatment may consist of the administration of a single dose or multiple doses of the compound of formula (I) or of a composition of the second embodiment. Usually, the treatment will consist of administering from one to five doses daily of the compound of formula (I) for a period of from one day to several years, up to the lifetime of the patient. Most usually, the treatment will consist of the administration of the compound of formula (I) for a period of from one day to one year.

The administered dosage of the compound of formula I can vary and depends on several factors, such as the condition of the patient. Dosages will range from 0.01 mg to 200 mg per kg. Usually, the dose of the active substance will be from 0.01 mg to 10 mg per kg of body weight.

Examples of dosage forms in accordance with the invention are as follows:

1. Tablet

| | |
|---|---|
| Compound of formula I | 0.01 to 20 mg, generally 0.1 to 10 mg |
| Starch | 10 to 20 mg |
| Lactose | 100 to 250 mg |
| Gelatin | 0 to 5 mg |
| Magnesium stearate | 0 to 5 mg |

2. Capsule

| | |
|---|---|
| Compound of formula I | 0.01 to 20 mg, generally 0.1 to 10 mg |
| Glycerol | 100 to 200 mg |
| Distilled water | 100 to 200 mg |
| Saccharin | 0 to 2 mg |
| Methyl Paraben | 1 to 2 mg |
| Polyvinylpyrrolidone | 0 to 2 mg |

3. Injectable solution

| | |
|---|---|
| Compound of formula I | 0.01 to 20 mg, generally 0.1 to 10 mg |
| Sodium chloride | 8.5 mg |
| Potassium chloride | 3 mg |
| Calcium chloride | 4.8 mg |
| Water for injection, q.s. to | 10 ml |

4. Elixir

| | |
|---|---|
| Compound of formula I | 0.01 to 20 mg, generally 0.1 to 10 mg |
| Sucrose | 100 mg |
| Glycerol | 2 ml |
| Carboxymethylcellulose | 20 mg |
| Cherry flavour | 2 mg |
| Water | q.s. to 10 ml |

EXAMPLES

Examples of compounds of formula (I) are those compounds of formula (IV) presented in Table 1:

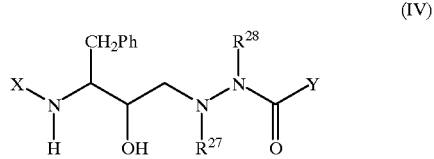

(IV)

TABLE 1
| No. | Example No. | X | R²⁷ | R²⁸ | Y |
|---|---|---|---|---|---|
| 1. | (8) | CBZ— | 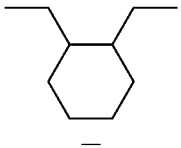 | | t-BuO— |
| 2a. | (10) | QC—Asn— | 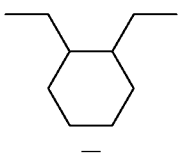 | | t-BuO— |
| 2b. | (23) | QC—Asn— | 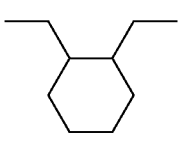 | | t-BuO— |
| 2b.A. | (23A) | QC—Asn— | 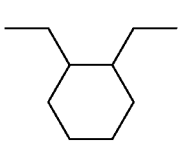 | | t-BuO— |
| 3. | (9) | QC—Val— | 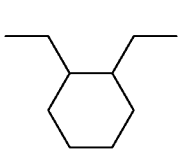 | | t-BuO— |
| 4. | (12) | QC—Gln— | 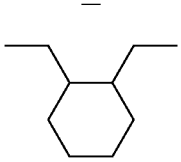 | | t-BuO— |
| 5. | (13) | QC—Thr— | 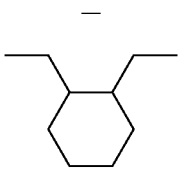 | | t-BuO— |
| 6. | (11) | PC—Val— | 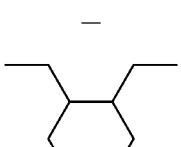 | | t-BuO— |
| 7A. | (3) | QC—Asn— | i-Pr— | H | t-BuO— |
| 7B. | (20) | QC—Asn— | i-Pr— | H | t-BuO— |
| 8. | (4) | QC—Asn— | i-Pr— | H | (2-PCNH)Ph— |
| 9. | (2) | QC—Val— | i-Pr— | H | t-BuO— |
| 10. | (16) | PC—Val— | 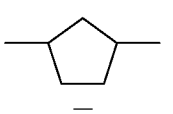 | | t-BuO— |

TABLE 1-continued

| No. | Example No. | X | R²⁷ | R²⁸ | Y |
|---|---|---|---|---|---|
| 11. | (18) | QC—Asn— | [2,6-disubstituted phenyl group] | | t-BuO— |
| 12. | (7) | QC—Asn— | [CH₃-CH(CH₂Ph)-CH₂- group] | H | t-BuO— |
| 13. | (25) | QC—Asn— | i-Pr— | H | t-Bu— |
| 14. | (26) | QC—Asn— | i-Pr— | H | t-BuNH— |
| 15. | (27) | PIC—Asn— | i-Pr— | H | t-BuO— |
| 16. | (30) | QC—Asn— | Bzl— | H | t-BuO— |
| 17. | (32) | QC—Asn— | cyclohexyl | H | t-BuO— |
| 18 | (35) | BZ—Asn— | i-Pr— | H | t-BuO— |
| 19. | (37) | QC—Asn— | —(CH₂)₄— | | t-BuO— |
| 20. | (38) | QC—CNAla— | [1,2-disubstituted cyclohexyl] | | t-BuO— |

In the above Table, CBZ refers to benzyloxycarbonyl; QC refers to quinoline-2-carbonyl; PC refers to 2-pyridinemethoxycarbonyl; Asn refers to asparagine; Val refers to valine; Gln refers to glutamine and Thr refers to threonine, BZ refers to benzoyl, PIC refers to picolinyl and CNAla refers to 3-cyano-L-alanine.

These compounds have the ability to inhibit HIV-1 and HIV-2 proteases and anti-HIV antiviral properties at the concentration from 10 nM to 100 $\mu$M in acutely infected MT 2 and peripheral blood lymphocytes. Compounds No. 2, 7B, 8 and 17 have shown a similar or increased ability to inhibit HIV to AZT (azidothymidine), with lower toxicity to the cells.

The HIV protease-inhibiting activity of representative compounds of the present invention has been tested by known methods (Brinkworth, R. I., et al., *Biochem. Biophys. Res. Commun.* 176, 241, (1991); McLeod, D. A., et al., *Bioorganic & Medicinal Chemistry Letters* (1991) 653–658). In this test, a number of compounds described in the examples hereinabove have been found to inhibit HIV-1 protease with half-maximal inhibition occurring at inhibitor concentrations (IC₅₀) of from sub nanomolar range to micromolar range, more typically, 3 nM to 30 $\mu$M.

The results of the above test compounds are presented in Table 2:

TABLE 2

HIV Protease-inhibiting Activity of Compounds of Formula (IV)

| Compound No | IC$_{50}$ (nM) |
|---|---|
| 2a | 5.4 ± 0.54 |
| 7A | 7.3 ± 0.7 |
| 7B | <3.5 |

TABLE 2-continued

HIV Protease-inhibiting Activity of Compounds of Formula (IV)

| Compound No | IC$_{50}$ (nM) |
|---|---|
| 10 | 3300 ± 650 |
| 11 | 12.5 ± 3.2 |

The antiviral activity of representative compounds of the present invention has been determined at the Antivirals Laboratory, Fairfield Hospital, Fairfield, Victoria, Australia. In this test a stock solution of each compound was made in DMSO, then diluted in culture medium (RF 10) to 2× the final concentration required for test. The final concentration of DMSO was 1% or below. Approximately 250,000 continuous lymphocytes of human origin (MT2 cells) or 750,000 human peripheral blood lymphocytes (PBLs) were exposed to dilutions of each test compound, then immediately infected with Human Immunodeficiency Virus type 1 (HIV) strain # 237228 (a clinical isolate obtained from a human source). The infectivity titers were expressed as tissue culture 50% infective dose (TCID$_{50}$ per ml) with 1 TCID$_{50}$ corresponding to the amount of supernatant required to infect 50% of the replicate cell cultures. The 250 and 200 TCID$_{50}$ were used for MT2 and PBL cells respectively. The cell/drug/virus mixture was then incubated at 37° C./CO$_2$ in a 24-well microtitre plate. Fresh amounts of the appropriate dilution of each drug were added to both MT2 and PBL cultures at day 3. At day 6, the extent of HIV-specific cytopathic effects (CPE) associated with each concentration of test compound in each of the cultures was rated according to the following scale:

| MT2 cells | PBLs |
|---|---|
| 4+: 75–100% of cells showing CPE | 3+: good CPE |
| 3+: 50–75% of cells showing CPE | 2+: moderate CPE |
| 2+: 25–50% of cells showing CPE | 1+: low CPE |
| 1+: 5–25% of cells showing CPE | trace: minimal CPE |
| +/−: less than 5% CPE | Negative: no CPE |
| Negative: no CPE | |

The activity of the compounds at each concentration was also assessed by their ability to inhibit viron-associated reverse transcriptase (RT) activity in the culture supernates. At the time of rating of CPE, supernatant fluids from each well were removed and RT activity measured using a standard assay. CPE ratings of negative, +/− (in MT2 cells) or trace (in PBLs), with greater than 95% inhibition of RT activity, was considered to represent $IC_{100}$ (the concentration of compound at which the virus replication is inhibited). Control cultures included in each test were:

(a) HIV-infected cells in the absence of test compound.
(b) Uninfected cells in the absence of tested compound.
(c) Cell toxicity control consisting of uninfected cells treated with dilutions of test compound.

At the conclusion of each experiment, viable cells in these cultures, as determined by tryptan blue exclusion, were compared with the counts obtained in (b), above. Only concentrations which were non-toxic (not resulting in viable cell counts significantly reduced to those found in (b)) were used in determining the antiviral index (AI) of each test compound. The ability of compounds 1–20 to block the spread of acute HIV infection in lymphocytic cell lines is shown in Table 3

TABLE 3

Anti-HIV-1 Antiviral Properties of Compounds 1–20.

| | MT2 Cells | | PBL Cells | |
|---|---|---|---|---|
| No. | $IC_{100}$ ($\mu M$) | AI | $IC_{100}$ ($\mu M$) | AI |
| 1. | 10[a] | 1 | nd | |
| 2a. | 0.1 | 50 | 0.1 | 100 |
| 2b. | 0.1 | 50 | 0.1 | 100 |
| 2b.A. | 0.01[b] | 100 | 0.01 | 1000 |
| 3. | 1 | 5 | 1 | 5 |
| 4. | 1 | 10 | 1 | 10 |
| 5. | 1 | <10 | 1 | <10 |
| 6. | 1 | <5 | 1 | <5 |
| 7A. | 1 | 50 | 1 | 25 |
| 7B. | 0.1 | 200 | 0.1 | >200 |
| 8. | 0.1 | >100 | 0.1 | >100 |
| 9. | 5 | 4 | nd | — |
| 10. | 25 | 1 | nd | — |
| 11. | 1 | >10 | nd | — |
| 12. | 1[b] | 10 | nd | — |
| 13. | 1 | 50 | 1 | >50 |
| 14. | 1 | 50 | 1 | >50 |
| 15. | 1 | 100 | 1 | 200 |
| 16. | 1 | 100 | 1 | 1 |
| 17. | 0.1 | 100 | 0.1 | 200 |
| 18. | 1 | 10 | 1 | >150 |
| 19. | 1 | 10 | 0.1 | 200 |
| 20. | 1 | 10 | 1 | 10 |

[a] $IC_{50}$;
[b] $IC_{80}$;
nd = not done.

In order to further illustrate the present invention, the following specific examples are given, it being understood that these are intended as illustrative only and are in no way limitative of the invention.

In these examples, melting points were taken on a hot stage apparatus and are uncorrected. Proton NMR spectra were recorded at 100 MHz or 300MHz on Perkin Elmer R32 or Bruker EM 300 spectrometers, respectively. Chemical shifts are ppm downfield from tetramethylsilane. Molecular weights of the compounds presented in Examples 1 to 23 were confirmed by electrospray mass spectrometry analysis, performed in the Department of Chemistry at La Trobe University, Melbourne. Thin layer chromotography (TLC) was performed on silica gel 60-F254 plates (Merck). Compounds were visualized by ultraviolet light and/or 2% aqueous potassium permanganate solution. The compositions (by volume) of the TLC solvent system were as follows: (A)= hexane/ethyl acetate 4:1; (B)=hexane/ethyl acetate 3:2; (C)= ethyl acetate; (D)=chloroform/methanol 23:2.

EXAMPLE 1 t-Butyl 3-isopropyl-[(2R,3S)-2-hydroxy-3-(phenylmethoxycarbonyl)amino-4-phenylbutyl] carbazate Step A: t-Butyl 3-isopropyl carbazate:

The title compound can be prepared by method of Dutta et al., *J.C.S. Perkin* 1 1975, 1712–1720 or by the following procedure: A mixture of 13.2 g (0.1 mol) of t-butyl carbazate and 6 g (0.103 mol) of acetone and 12.5 g (0.1 mol) of anhydrous magnesium sulfate in 100 ml of methylene chloride was stirred for 12 hr. at room temperature. After removal of the drying agent by filtration the filtrate was evaporated to dryness under reduced pressure to give 16.9 g (98% yield) of corresponding hydrazone melting 104–105° C. after crystallization from cyclohexane. To a suspension of 2.04 g (0.094 mol) of lithium borohydride in 100 ml of dry THF, 12 ml (0.094 mol) of chlorotrimethylsilane was added under nitrogen at room temperature. After 30 min. of stirring, 13.45 g (0.078 mol) of hydrazone was slowly added at room temperature and stirring was continued for 2 hr. Then 50 ml of methanol was carefully added and the mixture was evaporated to dryness under reduced pressure. The residue was partitioned between ether (150 ml) and water (50 ml). The organic phase was dried over anhydrous magnesium sulfate and filtered off. Dry hydrogen chloride was passed through the filtrate and the white solid formed was removed by filtration, washed with a fresh portion of ether and dried to give 10.5 g of hydrochloride salt of the title compound. This was transformed into a free base by partition between hexane (150 ml) and 20% aqueous potassium hydroxide. Yield 8.3 g (61%).

Step B: t-Butyl 3-Isopropyl-[(2R,3S)-2-hydroxy-3-(phenylmethoxy-carbonyl)amino-4-phenylbutyl]carbazate:

A mixture of 0.15 g (0.45 mmol) of N-CBZ-L-phenylalanine chloromethyl ketone and 1 ml of a saturated solution of sodium iodide in dry DMF was stirred for 15 min. at room temperature. To this, 0.074 9 (0.47 mmol) of t-butyl 3-isopropyl carbazate was added followed by 0.095 g (1.13 mmol) of sodium bicarbonate. After 6 hours of stirring at room temperature, 0.051 g (1.3 mmol) of sodium borohydride was added and stirring was continued for an additional 30 min. The solution was diluted to 30 ml with ethyl acetate and washed with 2% aqueous potassium bisulfate solution, water and saturated aqueous sodium chloride solution, and then dried over anhydrous magnesium sulfate. Evaporation of the solvent under reduced pressure and purificaton of the residue by flash chromatography (silica gel; hexane/ethyl acetate 20:5) gave the title compound, melting at 118–119.5° C., in 49% yield; R(A)=0.11; R (B)=0.47; NMR (CDCl$_3$) 1.0 (m, 6H, isopropyl CH$_3$); 1.44 (s, 9H, t-butyl CH$_3$); 2.62 (m, 2H, butyl CH$_2$-1); 2.75–3.2 (m, 3H, butyl CH-3, CH$_2$-4; 3.47 (m, 1H, isopropyl CH); 3.89 (m, 1H, butyl CH-2); 4.44 (broad s, 1H, OH); 4.6 (broad m, 1H, NH); 5.03 (s, 2H, methoxy CH$_2$); 5.3 (broad s, 1H, carbazate NH); 7.23 (m, 10H, aromatic).

EXAMPLE 2 t-Butyl 3-isopropyl-3-[(2R,3S)-2-hydroxy-3-(N-quinaldyl-L-valyl)amino-4-phenylbutyl]carbazate Step A: N-Quinaldyl-L-Valine:

A mixture of 0.62 g (3.6 mmol) of quinaldic acid and 0.61 g (3.76 mmol) of 1,1'-carbonyldiimidazole in 1 ml of dry 1,4-dioxane was stirred for 30 min at room temperature. To this, a solution of 0.43 g (3.7 mmol) of L-valine and 0.155 g (3.7 mmol) of lithium hydroxide in 1 ml of water was added and the resulting mixture was stirred vigorously at room temperature for about 4 hours. The mixture was diluted to 10 ml with water, cooled (ice-water bath), then acidified with 1N hydrochloric acid to pH about 3 and allowed to stand for 2 hours at 4° C. The crystals which formed were removed by filtration, washed three times with 5 ml of cold water and dried under high vacuum over phosphorus pentoxide to give 0.75 g of the product. Yield= 76%, melting point 134–136° C., NMR (DMSO-d$_6$) 1.03 (d, 6H, val CH$_3$); 2.3 (m, 1H, val CH-β); 3.35 (broad s, 1H, OH); 4.49 (q, 1H, val CH-α); 7.5–8.3 (m, 5H, aromatic); 8.5–8.76 (m, 2H, aromatic, NH).

Step B: t-Butyl 3-isopropyl-3-[(2R,3S)-3-amino-2-hydroxy-4-phenylbutyl]carbazate:

To a chilled solution of 0.113 g (0.24 mmol) of the product of Example 1 in 2 ml of methanol was added 0.1 g of 10% palladium on activated carbon under nitrogen, followed by 0.1 g of sodium borohydride. The reaction was allowed to warm to room temperature and stir for 1 hour, then catalyst was removed by filtration and washed with fresh portion of methanol. The combined filtrates were treated with 1 ml of 0.1 N aqueous solution of hydrochloric acid and evaporated to dryness under reduced pressure. The residue was treated with 5 ml of 0.1 N potassium hydroxide and the product was taken up with 30 ml of diethyl ether. The organic phase was washed with saturated aqueous sodium chloride solution, dried over anhydrous magnesium sulfate and evaporated under reduced pressure to give 0.0797 g (99% yield) of the Step B product, which was used in the next step without further purification.

Step C: t-Butyl 3-isopropyl-3-[(2R,3S)-2-hydroxy-3-(N-quinaldyl-L-valyl)-amino-4-phenylbutyl]carbazate:

To a mixture of 0.0643 g (0.24 mmol) of the acid from Step A, 0.0797 g (0.236 mmol) of the the amine from Step B, 0.032 g (0.24 mmol) of 1-hydroxybenzotriazole in 0.5 ml of anhydrous DMF was added 0.071 g (0.24 mmol) of 1-(3-dimethylaminopropyl)-3-ethyl-carbodiimide methiodide. After stirring overnight at room temperature the mixture was diluted to 30 ml with ethyl acetate and washed successively with water, 5% aqueous sodium bicarbonate, 2% aqueous potassium bisulfate solution, and saturated sodium chloride solution and dried over anhydrous magnesium sulfate. Evaporation of the solvent under reduced pressure and purification of the residue by column chromatography (silica gel, hexane/ethyl acetate 3:2) gave 0.091 g (65% yield) of the title compound, melting at 186–189° C.: R$_f$(B)=0.19; R$_f$(C)=0.83; NMR (CDCl$_3$) 1.0 (m, 12H, val and isopropyl CH$_3$); 1.71 (s, 9H, t-butyl CH$_3$); 2.3 (m, 1H, val CH-β); 2.5–3.27 (m, 3H, butyl CH-3, CH$_2$); 3.5 (m, 1H, isopropyl CH); 4.31 (m, 2H, val CH-α, OH); 5.43 (broad s, 1H, carbazate NH); 6.22 (broad d, 1H, butyl NH); 6.7–8.73 (m, 12H, aromatic, NH).

EXAMPLE 3 t-Butyl 3-isopropyl-3-[(2R,3S)-2-hydroxy-3-(N-quinaldyl-L-asparaginyl)amino-4-phenylbutyl]carbazate Step A: N-Quinaldoyl-L-asparagine:

When L-asparagine was substituted for L-valine in Step A of Example 2, the identical process afforded the title compound, melting at 200–203° C., in 85% yield, NMR (DMSO-d$_6$) 3.0 (m, 2H, asn CH$_2$); 5.0 (m, 1H, asn CH-α); 6.3 (broad s, 1H, OH); 6.55 (broad s, 1H, NH$_2$); 7.3 (broad s, 1H, NH$_2$); 7.55–8.6 (m, 6H, aromatic); 9.22 (d, 1H, NH).

Step B: t-Butyl 3-isopropyl-3-[(2R,3S)-2-hydroxy-3-(N-quinaldyl-L-asparaginyl)amino-4-phenylbutyl]carbazate:

To a stirred solution of the product of Step A (0.111 g; 0.386 mmol), the product of Example 2, Step B (0.13022 g; 0.386 mmol), benzotriazol-1-yloxytris(dimethyl-amino)-phosphonium hexafluorophosphate (0.205 g; 0.46 mmol) and 1-hydroxy-benzotriazole (0.052 g; 0.384 mmol) in 1 ml of anhydrous DMF was added, N,N-diisopropylethylamine (0.24 ml; 1.38 mmol). After stirring for 12 hours at room temperature the reaction was diluted to 30 ml with ethyl acetate and washed with water, 2% potassium bisulfate, 5% sodium bicarbonate and saturated aqueous sodium chloride solution and dried over anhydrous magnesium sulfate. Evaporation of the solvent under reduced pressure and purification of the residue by column chromatography (silica gel, ethyl acetate) gave 0.152 g (65% yield) of the title product melting at 109–114° C.; R$_f$(C)=0.36; R$_f$(D)=0.37; NMR (CDCl$_3$) 1.0 (m, 6H, val, isopropyl CH$_3$); 1.42 (s, 9H, t-butyl CH$_3$); 2.5–3.1 (m, 7H, asn CH$_2$, butyl CH$_2$-1, -4, CH-3); 3.44 (m, 1H, isopropyl CH); 4.21 (m, 1H, butyl CH-2); 4.55 (s, 1H, OH); 4.94 (m, 1H, asn CH-α); 5.4–6.2 (m, 3H, amide); 6.7–8.4 (m, 11H, aromatic); 9.25 (m, 1H, NH).

EXAMPLE 4

1-(2-pyridyl)methoxycarbonylanthranilyl-2-[(2R,3S)-2-hydroxy-3-(N-quinaldyl-L-asparaginyl)amino-4-phenylbutyl]-2-isopropyl-hydrazine Step A: (2-Pyridyl)methoxycarbonylanthranilic acid:

Phosgene was bubbled through a solution of 10 g (66 mmol) of methylanthranilate in 15 ml of anhydrous toluene for 2 hours at reflux. Then the solvent was distilled off under reduced pressure to give 11.7 g (100%) of 2-methoxycarbonylphenyl-isocyanate; NMR (CDCl$_3$) 3.89 (s, 3H, CH$_3$); 7.0–7.63 (m, 3H, phenyl H-3, -4, -5); 8.0 (dd, 1H, phenyl H-6). This was converted to the title compound, in 34% overall yield, by condensation with an equimolar amount of 2-pyridylcarbinol followed by saponification of the resulting ester with 1 N sodium hydroxide and acidification of the reaction mixture to pH 4. The crude product was purified by crystallization from ethyl acetate; melting point=172–175° C.; NMR (DMSO-d$_6$) 5.2 (s, 2H, methoxy CH$_2$); 6.8–8.8 (m, 9H, aromatic, NH); 10.8 (broad s, 1H, OH).

Step B: 2-[(2R,3S)-2-hydroxy-3-(N-quinaldyl-L-asparaginyl)amino-4-phenylbutyl]-2-isopropyl-hydrazine:

Hydrogen chloride gas was bubbled through the solution of 0.1 g (0.165 mmol) of product of Example 3 in 10 ml of 1% solution of methanol in methylene chloride for 30 min at room temperature. After washing the excess of HCl with nitrogen the solvent was removed under reduced pressure to give 0.089 g (100%) of the title compound as a white solid.

Step C: 1-(2-pyridyl)methoxycarbonylanthraniloyl-2-[(2R,3S)-2-hydroxy-3-(N-quinaldyl-L-asparaginyl)amino-4-phenylbutyl]-2-isopropyl-hydrazine:

Coupling the products of Step A and B, using the general procedure outlined in Example 3, Step B, gave the title compound in 24% yield, after purification by column chromatography (silica gel, ethyl acetate); melting point= 96–112° C.; $R_f(C)=0.13$ ; $R_f(D)=0.36$; NMR (CDCl$_3$) 1.18 (m, 6H, isopropyl CH$_3$); 1.8–3.4 (m, 8H, asn CH$_2$, butyl CH$_2$-1, -4, CH-3, OH); 3.6 (m, 1H, isopropyl CH); 4.2 (m, 1H, butyl CH-3); 4.5–5.18 (m, 2H, asn CH-α, hydrazide NH); 5.35 (s, 2H, methoxy CH$_2$); 5.3–6.5 (broad m, 2H, asn NH$_2$); 6.8–8.8 (m, 20H, aromatic, butyl NH); 9.14 (m, 1H, asn NH); 10.36 (s, 1H, anthr. NH).

EXAMPLE 5 t-Butyl 3-isopropyl-3-[(2-oxo-3(S)-(N-quinaldyl-L-asparaginyl)amino-4-phenylbutyl]carbazate To a mixture of 0.0533 g (0.088 mmol) of the product of Example 3 and 0.049 9 (0.31 mmol) of sulfur trioxide pyridine complex in 1 ml of anhydrous DMSO 0.043 ml (0.31 mmol) of triethylamine was added. After stirring for 45 min at room temperature the reaction mixture was poured on ice and allowed to warm to room temperature. The precipitate which formed was removed by filtration, washed with water and dried overnight in vacuo to give 0.044 g (83% yield) of the title compound which was further purified by crystallization from the aqueous methanol; melting point=146–150° C.; $R_f(D)=0.32$; NMR (CDCl$_3$) 1.0 (d, 6H, isopropyl CH$_3$); 1.38 (s, 9H, t-butyl CH$_3$); 2.5–3.3 (m, 5H, asn CH$_2$, butyl CH$_2$, isopropyl CH); 3.7 (s, 2H, butyl CH$_2$); 4.6–5.3 (m, 2H, asn CH, butyl CH-3); 5.6 (broad s, 1H, NH); 6.09 (broad m, 2H, 2× NH); 6.9–8.4 (m, 12H, aromatic, NH); 9.2 (broad d, 1H, asn NH).

EXAMPLE 6 t-Butyl 3-(1-methyl-3-phenylpropen-3-yl)-3-[(2R and S, 3S)-2-hydroxy-3-(phenylmethoxycarbonyl)amino-4-phenylbutyl]carbazate Step A: 2(R,S)-3(S)-1,2-Epoxy-3-phenylmethoxycarbonylamino-4-phenyl-butane:

To the solution of 6 g (18 mmol) of N-CBZ-L-phenylalanine chloromethyl ketone in 30 ml of 50% methanolic tetrahydrofuran was added 0.68 g of sodium borohydride. After stirring for 30 min at room temperature the mixture was carefully acidified with 1N hydrochloric acid and evaporated to dryness under reduced pressure. The residue was diluted to 50 ml with methylene chloride, washed with water and saturated aqueous sodium chloride and dried over anhydrous magnesium sulfate. Evaporation gave 6.02 g (100%) of 2(R,S)-3(S)-1-chloro-2-hydroxy-3-phenylmethoxycarbonylamino-4-phenylbutane, as a white solid. This was dissolved in 50 ml of isopropanol and 9 ml of 2N methanolic potassium hydroxide was added at room temperature. After stirring for 1 hour at room temperature the solvent was removed under reduced pressure and the residue was partitioned between 50 ml of ethyl acetate and 20 ml of water. The organic phase was washed with saturated aqueous sodium chloride, dried over anhydrous magnesium sulfate and evaporated to dryness to give 5.3 g (99% yield) of the title compound as the predominantly 2(S) stereoisomer as determined from relative integration of erythro-NCH (3.74 ppm; 72%) and threo-NCH (4.2; 28%); NMR (CDCl$_3$) 2.42–3.17 (m, 5H, butane CH$_2$-1, -4, CH-2); 3.74 (m, 0.72H, butane CH-3); 4.2 (m, 0.28H, butane CH-3); 4.73 (broad m, 1H, NH); 5.08 (s, 2H, methoxy CH$_2$); 7.3 (m, 10H, aromatic).

Step B: t-Butyl 3-(1-methyl-3-phenylpropen-2-yl) carbazate:

This compound was prepared by the method of Ghali et al. (J. Org. Chem., 1981, 46, 5413–5414) in about 65% overall yield, from trans-4-phenyl-3-buten-2-one and t-butyl carbazate, after crystallization of the crude product from hexane; melting point=76–79° C.; NMR (CDCl$_3$) 1.24 (d, 3H, CH$_3$); 1.45 (s, 9H, t-butyl CH$_3$); 3.78 (m, 2H, propenyl CH-1, carbazate NH-3); 5.8–6.29 (m, 2H, carbazate NH-2, propenyl CH-2); 6.53 (d, 1H, propenyl CH-3); 7.3 (m, 5H, aromatic).

Step C: t-Butyl 3-(1-methyl-3-phenylpropen-3-yl)-3-[(2R and S, 3S)-2-hydroxy-3-(phenylmethoxycarbonyl)amino-4-phenylbutyl]carbazates:

0.57 g of epoxide from Step A in about 15 ml of anhydrous ether was added at room temperature to a vigorously stirred suspension of 8 g of alumina (E. Merck I) impregnated with 1 g (3.81 mmol) of the product of Step B. The stirring was continued for 16 hours and the catalyst was removed by filtration and washed with ethyl acetate (3×25 ml). The combined filtrates were evaporated to dryness under reduced pressure and the residue was separated and purified by column chromatography (silica gel, hexane/ethyl acetate 4:1). The product fractions were evaporated in vacuo to give the 2R,3S isomer (0.298 g; 28%) and the 2S,3S isomer (0.1 g; 9%) of the title compound as a white solid.

Isomer 2R,3S: melting point=101–104° C.; $R_f(A)=0.19$; NMR (CDCl$_3$) 1.27 (dd, 3H, CH$_3$); 1.42 (s, 9H, t-butyl CH$_3$); 2.67 (m, 2H, butyl CH$_2$-1); 3.0 (m, 2H, butyl CH$_2$-4); 3.5 (m, 2H, propenyl CH-1, butyl CH-3); 3.91 (m, 1H, butyl CH-2); 4.4, 4.82, 5.38 (broad multiplets, 3×H, amide NH, OH); 5.0 (s, 2H, methoxy CH$_2$) 6.09 (dd, 1H, propenyl CH-2); 6.5 (d, 1H, propenyl CH-3); 7.22 (m, 15H, aromatic). Isomer 2S,3S: melting point=128–130° C.; $R_f(A)=0.26$; NMR (CDCl$_3$) 1.22 (m, 3H, CH$_3$); 1.4 (s, 9H, t-butyl CH$_3$); 2.55 (broad m, 2H, butyl CH$_2$-1); 2.95 (d, 2H, butyl CH$_2$-4); 3.5 (m, 3H, propenyl CH-2, butyl CH-2,-3); 4.44 (m, 1H, OH); 5.05 (m, 2H, methoxy CH2); 5.34 (m, 2H, NH); 6.08 (dd, 1H, propenyl CH-2); 6.5 (d, 1H, propenyl CH-3); 7.3 (m, 15H, aromatic).

EXAMPLE 7 t-Butyl 3-(1-methyl-3-phenylpropyl)-3-[(2R,3S)-2-hydroxy-3-(N-quinaldyl-L-asparaginyl)amino-4-phenylbutyl]carbazate Step A: t-Butyl 3-(1-methyl-3-phenylpropyl)-3-[(2R,3S)-2-hydroxy-3-amino-4-phenylbutyl]carbazate:

This was prepared in 98% yield by hydrogenolysis of the isomer 2R,3S of the product of Example 6, Step C, performed as described in Example 2, Step B, as white solid.

Step B: t-Butyl 3-(1-methyl-3-phenylpropyl)-3-[(2R,3S)-2-hydroxy-3-(N-quinaldyl-L-asparaginyl)amino-4-phenylbutyl]-carbazate:

The condensation of the amine from Step A (0.0835 9; 0.195 mmol) with N-quinaldyl-L-asparagine (Example 3, Step A) (0.0563 g; 0.196 mmol), under condition given in Step B of Example 3, gave 0.11 g (81% yield) of the title compound after purification by column chromatography (silica gel, chloroform/methanol 23:2); melting point =141–143° C.; $R_f(C)$=0.53, $R_f(D)$=0.38; NMR (CDCl$_3$) 0.7–2.1 (m, 15H, CH$_3$, t-butyl CH$_3$, propyl CH$_2$-2, OH); 2.4–3.26 (m, 8H, butyl CH$_2$-1, -4, asn CH$_2$, propyl CH$_2$-3); 3.5 (m, 1H, propyl CH-1); 4.22 (m, 1H, butyl CH-3); 4.7 (m, 1H, carbazate NH); 4.95 (m, 1H, asn CH-α); 5.24–6.4 (m, 3H, NH$_2$, NH); 6.5–8.5 (m, 16H, aromatic); 9.14 (d, 1H, asn NH).

EXAMPLE 8 cis-1,6-3-t-Butoxycarbonyl-4-[(2RS,3S)-2-hydroxy-3-(phenylmethoxycarbonyl)amino-4-phenylbutyl]-3,4-diaza-bicyclo-[4.4.0]decane Step A: cis-1,6-3-t-Butoxycarbonyl-3,4-diaza-bicyclo[4.4.0]-decane:

Cis-1,2-cyclohexanedimethanol was converted quantitatively to cis-1,2-cyclohexanedimethyliodide by the general method (*Vogel's Textbook of Practical Organic Chemistry*, 4th Ed. p. 393, Longman Group Limited, London 1978). An alkylation of 1-benzyloxycarbonyl-2-t-butoxycarbonylhydrazine (Dutta et al., J.C.S. Perkin I, 1975, 1712–1720) with cis-1,2-cyclohexanedimethyliodide, in the presence of two equivalents of sodium hydride by the method of Dutta et al (J.C.S. Perkin I, 1975, 1712–1720) gave cis-1,6-4-benzyloxycarbonyl-3-t-butoxycarbonyl-3,4-diazabicyclo[4.4.0]-decane in 24% yield, after purification on column chromatography (silica gel, hexane); melting point=68–69.5° C.; NMR (CDCl$_3$) 1.0–2.2 (m, 19H, CH$_2$-7,8,9,10, CH-1,6); 3.15 (m, 2H, CH$_2$-5); 3.82 (m, 2H, CH$_2$-2); 5.11 (m, 2H, benzyl CH$_2$);7.3 (s, 5H, aromatic). This was converted to the title compound in 95% yield by hydrogenolysis, performed as described in Example 2, Step B; melting point=55–63° C.; NMR (CDCl$_3$) 1.0–2.05 (m, 19H, CH$_2$-7,8,9,10, CH-1,6); 2.82 (m, 2H, CH$_2$-5); 3.33 (m, 2H, CH$_2$-2), 4.0 (broad s, 1H, NH).

Step B: cis-1,6-3-t-Butoxycarbonyl-4-[(2RS,3S)-2-hydroxy-3-(phenylmethoxycarbonyl)amino-4-phenylbutyl]-3,4-diaza-bicyclo-[4.4.0]decane:

When the product of Step A was substituted for t-butyl 3-(1-methyl-3-phenylpropen-2-yl)carbazate in Example 6, Step C, the identical process afforded the title compound, melting at 98–103° C., in 42% yield, after purification on column chromatography (silica gel, hexane/ethyl acetate 4:1); $R_f(A)$=0.2, 0.3; $R_f(B)$=0.55, 0.63; NMR (CDCl$_3$) 1.0–2.18 (m, 19H, decane CH$_2$-7,8,9,10, CH-1,6, t-butoxy CH$_3$); 2.42 (m, 2H, decane CH$_2$-5); 2.78–4.5 (m, 9H, butyl CH$_2$-1,4, CH-2,3, decane CH$_2$-2, OH); 4.8 (broad m, 1H, NH); 5.0 (s, 2H, methoxy CH$_2$); 7.22 (m, 10H, aromatic).

EXAMPLE 9 cis-1,6-3-t-Butoxycarbonyl-4-[(2RS,3S)-2-hydroxy-3-(N-quinaldyl-L-valyl)-amino-4-phenylbutyl]-3,4-diaza-bicyclo[4.4.0]decane When the product of Example 8 is substituted for t-Butyl 3-isopropyl-3-[(2R,3S)-2-hydroxy-3-(phenylmethoxycarbonyl)amino-4-phenylbutyl]carbazate in Example 2, the identical process afforded the title compound in 52% yield, after purification by column chromatography (silica gel, hexane/ethyl acetate 3:2); melting point=95–101° C.; $R_f(B)$=0.32; $R_f(C)$=0.85; NMR (CDCl$_3$) 0.64–1.93 (m, 25H, val CH$_3$, decane CH$_2$-7,8,9,10, CH-1,6, t-butoxy CH$_3$); 2.38 (m, 3H, decane CH$_2$-5, val CH-β); 2.73–3.82 (m, 7H, decane CH$_2$-2, butyl CH$_2$-1,4, CH-3); 3.82–5.35 (m, 3H, val CH-α, butyl CH-2, OH); 6.0–9.0 (m, 13H, aromatic, NH).

EXAMPLE 10 cis-1,6-3-t-Butoxycarbonyl-4-[(2RS,3S)-2-hydroxy-3-(N-quinaldyl-L-asparaginyl)amino-4-phenylbutyl]-3,4-diaza-bicyclo[4.4.0]decane According to Example 2, Step B, the product of Example 8 was converted quantitatively to cis-1,6-3-t-butoxycarbonyl-4-[(2RS,3S)-2-hydroxy-3-amino-4-phenylbutyl]-3,4-diaza-bicyclo[4.4.0]decane. This material was coupled with N-quinaldyl-L-asparagine (Example 3, Step A) by process identical to Example 3, Step B to give the title compound in 52% yield; melting point=111–114° C.; $R_f(C)$=0.44; $R_f(D)$=0.46; NMR (CDCl$_3$) 1.0–2.2 (m, 19H, decane CH$_2$-7,8,9,10, CH-1,6, t-butoxy CH$_3$); 2.2–3.83 (m, 11H, decane CH$_2$-2,5, butyl CH$_2$-1,4, CH-3); 4.13 (m, 2H, butyl CH-2, OH); 4.95 (m, 1H, asn CH); 5.73, 6.24 (s, s, 2H, NH$_2$); 6.7–7.33 (m, 6H, aromatic, NH); 7.4–8.42 (m, 6H, aromatic); 9.2 (broad m, 1H, NH).

EXAMPLE 11 cis-1,6-3-t-Butoxycarbonyl-4-[(2RS,3S)-2-hydroxy-3-[N-(2-pyridyl)-methoxycarbonyl-L-valyl]amino-4-phenylbutyl]-3,4-diaza-bicyclo[4.4.0]decane Step A: N-(2-Pyridyl)methoxycarbonyl-L-valine:

An equimolar mixture of (2-pyridyl)carbinol (3 g) and methyl L-2-isocyanato-3-methylbutanoate (4.32 g) (Fankhauser P. et al., Helv. Chim. Acta, 1970, 2298–2313) was stirred for 12 hours at 80–90° C. under nitrogen to give 7.32 g (100%) of N-(2-pyridyl)methoxycarbonyl-L-valine methyl ester as a colorless syrup; NMR (CDCl$_3$) 0.94 (m, 3H, val CH$_3$); 2.17 (m, 1H, val CH-β); 3.71 (s, 3H, OCH$_3$); 4.27 (m, 1H, val CH-α); 5.18 (s, 2H, CH$_2$); 5.43 (m, 1H, NH); 6.85–7.82 (m, 3H, aromatic); 8.45 (m, 1H, aromatic). This was diluted to 25 ml with methanol and 6.04 ml of 5 M aqueous potassium hydroxide was added. The resulting mixture was stirred for 1 hour at reflux, then cooled to room temperature and evaporated to dryness in vacuo. The residue was diluted to 25 ml with water and washed with ether. The aqueous phase was cooled in an ice bath and acidified to pH=5 and allowed to stay overnight at 4° C. The resultant precipitate was filtered off, washed with small portions of cold water (3×15 ml) and dried in vacuo over phosphorous pentoxide to give 4.92 g (71% yield) of the title compound melting at 116–118° C.; NMR (DMSO-d$_6$) 0.93 (d, 6H, val CH$_3$); 2.1 (m, 1H, val CH-β); 3.4 (broad s, 1H, OH); 3.93 (m, 1H, val CH-α); 5.13 (s, 2H, CH$_2$); 7.17–8.0 (m, 4H, aromatic, NH); 8.5 (m, 1H, aromatic).

Step B: cis-1,6-3-t-Butoxycarbonyl-4-[(2RS,3S)-2-hydroxy-3-[N-(2-pyridyl)methoxycarbonyl-L-valyl]amino-4-phenylbutyl]-3,4-diaza-bicyclo-[4.4.0]decane:

When the product of Step A is substituted for N-quinaldyl-L-asparagine in Example 10, the identical process afforded the title compound, melting at 82–87° C., in 38% yield after purification under the conditions given in Example 9; $R_f(B)$=0.08; $R_f(C)$=0.64; $R_f(D)$=0.66; NMR (CDCl$_3$) 0.82 (m, 6H, val CH$_3$); 1.05–2.73 (m, 22H, decane CH$_2$-5,7,8,9,10, CH-1,6, t-butoxy CH$_3$, val CH-β); 2.73–4.6 (m, 9H, butyl CH$_2$-1,4, CH-2,3, decane CH$_2$-2, val CH-α); 5.05–5.5 (m, 3H, CH$_2$, OH); 5.5–6.78 (m, 2H, NH); 7.0–7.9 (m, 8H, aromatic); 8.57 (m, 1H, aromatic).

EXAMPLE 12 cis-1,6-3-t-Butoxycarbonyl-4-r(2RS,3S)-2-hydroxy-3-(N-quinaldyl-L-glutaminyl)amino-4-phenylbutyl]-3,4-diaza-bicyclo[4.4.0]decane Step A: N-Quinaldyl-L-Glutamine:

When L-glutamine was substituted for L-valine in Step A of Example 2, the identical process afforded the title compound, melting at 188–190° C., in 72% yield; NMR (CDCl$_3$/DMSO-d$_6$ 1:1) 2.34 (m, 4H, gln CH$_2$); 4.7 (m, 1H, gln CH-α); 6.3, 7.15 (broad ss, 2H, NH$_2$); 7.4–8.51 (m, 7H, aromatic OH); 8.82(d, 1H, NH).

Step B: cis-1,6-3-t-Butoxycarbonyl-4-[(2RS,3S)-2-hydroxy-3-[N-quinaldyl-L-glutaminyl]amino-4-phenylbutyl]-3,4-diaza-bicyclo[4.4.0]decane:

When the product of Step A is substituted for N-quinaldyl-L-asparagine in Example 10, the identical process afforded the title compound, melting at 106–115° C., in 18% yield; R$_f$(C)=0.27; R$_f$(D)=0.30; NMR (CDCl$_3$) 0.8–2.7 (m, 26H, decane CH$_2$-7,8,9,10, CH-1,6, gln CH$_2$, t-butoxy CH$_3$, butyl CH-3); 2.7–3.8 (m, 6H, decane CH2-2,5, butyl CH$_2$-4); 4.36 (m, 1H, butyl CH-2); 4.6 (m, 1H, gin CH); 5.1 (broad s, 1H, OH); 5.4 (m, 1H, NH); 6.07, 6.6 (d,d, 2H, NH$_2$); 6.8–8.5 (m, 11H, aromatic); 8.8 (m, 1H, gin NH).

EXAMPLE 13 cis-1,6-3-t-Butoxycarbonyl-4-[(2RS,3S)-2-hydroxy-3-(N-quinaldyl-L-threonyl)-amino-4-phenylbutyl]-3,4-diaza-bicyclo[4.4.0]decane Step A: N-Quinaldoyl-L-threonine:

When L-threonine was substituted for L-valine in Step A of Example 2, the identical process afforded the title compound, melting at 184–185° C., in 74% yield; NMR (CDCl3/DMSO-d$_6$ 1:1) 1.29 (m, 3H, CH$_3$); 4.5 (m, 1H, thr CHβ); 4.68 (dd, 1H, thr CH-α); 7.4–9.27 (m, 9H, aromatic, acid OH, 2-OH, NH).

Step B: cis-1,6–3-t-Butoxycarbonyl-4-[(2RS,3S)-2-hydroxy-3-(N-quinadyl-L-threonyl)amino-4-phenylbutyl]-3,4-diaza-bicyclo[4.4.0]decane:

When the product of Step A is substituted for N-quinaldyl-L-asparagine in Example 10, the identical process afforded the title compound, melting at 102–112° C., in 36% yield, R$_f$(C)=0.72; R$_f$(D)=0.61, 0.7; NMR (CDCl$_3$) 1.0–2.75 (m, 25H, t-butoxy CH$_3$, decane CH$_2$-7,8,9,10, CH-1,6, butyl CH$_2$-4, OH); 2.75–4.0 (m, 8H, decane CH$_2$-2,5, butyl CH$_2$-4, OH); 4.0–4.7 (m, 3H, thr CH-α, butyl CH-3); 6.5–7.4 (m, 6H, aromatic, NH); 7.4–8.5 (m, 6H, aromatic); 8.8 (m, 1H, thr NH).

EXAMPLE 14

2-t-Butoxycarbonyl-3-[(2RS,3S)-2-hydroxy-3-(phenylmethoxycarbonyl)amino-4-phenylbutyl]-2,3-diaza-bicyclo[2.2.1]hept-5-ene Step A: 2-t-Butoxycarbonyl-3-phenylmethoxycarbonyl-2,3-diaza-bicyclo-[2.2.]hept-5-ene:

To a stirred mixture of 1 g (4.34 mmol) of 1-benzyloxycarbonyl-2-t-butoxycarbonylhydrazine (Dutta et al., J.C.S. Perkin I, 1975, 1712–1720) in 30 ml of anhydrous methylene chloride 1.55 g (8.7 mmol) of N-bromosuccinimide was added at 0° C. and the stirring was continued for 1 hour with external cooling in an ice bath. The reaction mixture was washed with 10% aqueous sodium thiosulfate solution and saturated aqueous sodium chloride solution, dried over anhydrous magnesium sulfate and evaporated to dryness in vacuo. The residue was redissolved in 15 ml of anhydrous ether, 0.57 g (8.7 mmol) of freshly distilled cyclopentadiene was added and the mixture was allowed to stay for 1 hour at room temperature. Evaporation to dryness under reduced pressure gave 0.77 g (54% yield) of the title product as a colorless syrup; NMR (CDCl$_3$) 1.44 (s, 9H, t-butoxy CH$_3$); 1.7 (m, 2H, CH2-7); 5.06 (m, 2H, CH-1,4); 5.15 (s, 2H, methoxy CH$_2$); 6.4 (m, 2H, CH-5,6); 7.24 (m, 5H, aromatic).

Step B: 2-t-Butoxycarbonyl-3-[(2RS,3S)-2-hydroxy-3-(phenylmethoxycarbonyl)amino-4-phenylbutyl]-2,3-diaza-bicyclo[2.2. 1]-hept-5-ene:

A mixture of 0.2 g (0.6 mmol) of the product of Step A and 0.8 ml of 1N aqueous solution of potassium hydroxide in 5 ml of methanol was refluxed under nitrogen for 4 hours. The resulting mixture was partially evaporated, diluted to 10 ml with water and extracted with diethyl ether (3×10 ml). The combined organic phase was washed with saturated aqueous sodium chloride solution, dried over anhydrous magnesium sulfate and evaporated to dryness. The residue was purified by column chromatography (silica gel; hexane/ethyl acetate 3:2) to give 0.05 g (42% yield) of 2-t-butoxycarbonyl-2,3-diaza-bicyclo[2.2.1]hept-5-ene. This material (0.049 g, 0.25 mmol) was dissolved in 2 ml of isopropanol containing 0.0744 g (0.25 mmol) of 2(R,S)-3(S)-1,2-epoxy-3-phenylmethoxycarbonylamino-4phenylbutane (Step A of Example 6) and the resulting mixture was stirred for 15 hours at 80±5° C. under nitrogen. The mixture was cooled to room temperature, evaporated to dryness in vacuo and purified by column chromatography (silica gel hexane/ethyl acetate 4:1) to give 0.054 g (44% yield) of title product; melting point=111–113° C.; R$_f$(A)=0.07; R$_f$(B)=0.31; NMR (CDCl$_3$) 1.43 (s, 9H, t-butoxy CH$_3$); 1.8 (m, 2H, CH$_{2-7}$); 2.4–3.15 (m, 4H, butyl CH$_2$-1,4); 3.2–4.2 (m, 3H, butyl, CH-2,3, OH); 4.5–5.33 (m, 5H, CH-1,4, methoxy CH$_2$, NH); 6.2–6.6 (m, 2H, CH-5,6); 7.2 (m, 1OH, aromatic).

EXAMPLE 15

2-t-Butoxycarbonyl-3-[(2RS,3S)-2-hydroxy-3-(phenylmethoxycarbonyl)amino-4-phenylbutyl]-2,3-diaza-bicyclo[2.2.1]heptane When the product of Step A of Example 14 is substituted for cis-1,6-4-benzyloxy-carbonyl-3-t-butoxycarbonyl-3-4-diaza-bicyclo[4.4.0]decane in Example 8, a similar process afforded the title compound in 31% yield; melting point= 119–126° C.; R$_f$(A)=0.12; R$_f$(B)=0.34, 0.39; NMR (CDCl$_3$) 1.2–2.1 (m, 15H, t-butoxy CH$_3$, CH$_2$-5,6,7); 2.5–3.2 (m, 4H, butyl CH$_2$-1,4); 3.2–4.4 (m, 4H, butyl CH-2,3, CH-1,6); 4.7–5.5 (m, 4H, methoxy CH$_2$, NH, OH); 7.26 (m, 10H, aromatic).

EXAMPLE 16

2-t-Butoxycarbonyl-3-[(2RS, 3S)-2-hydroxy-3-[N-(2-pyridyl)-methoxycarbonyl-L-valyl]amino-4-phenylbutyl]-2,3-diaza-bicyclo[2.2.1]-heptane According to Example 2, Step B the product of Example 15 was converted quantitatively to 2-t-butoxycarbonyl-3-[(2RS, 3S)-3-amino-2-hydroxy-4-phenylbutyl]- 2,3-diaza-bicyclo[2.2.1]heptane. This material was coupled to N-(2-pyridyl)methoxycarbonyl-L-valine (Example 11, Step A) by process identical to Example 3, Step B to give the title compound in 51% yield: melting point=73–77° C.; R$_f$(C)= 0.45; R$_f$(D)=0.49; NMR (CDCl$_3$) 0.7–1.0 (m, 6H, val CH$_3$);

1.25–2.15 (m, 16H, t-butoxy $CH_3$, val CH-β, $CH_2$-5,6,7); 2.55–3.1 (m, 4H, butyl $CH_2$-1,4); 3.3–3.7 (butyl CH-2,3); 3.91 (m, 1H, val CH-α); 4.1–4.4 (m, 2H, CH-1,4); 4.9–5.4 [m, 4H, methoxy $CH_2$ (s, 5.26), OH, NH]; 6.6 (m, 1H, NH); 7.26, 7.7, 8.57 (m, 7H, 1H, 1H, aromatic).

EXAMPLE 17

2-[N-(1S)(2-methyl-1-methoxycarbonylpropyl) carbamoyl]-3-[(2RS,3S)-2-hydroxy-3-[N-(2-pyridyl) methoxy-L-valyl]amino-4-phenylbutyl]-2,3-diaza-bicyclo[2.2.0]heptane According to Example 4, Step B, the product of Example 16 was converted quantitatively to the hydrochloride salt of 3-[(2RS, 3S)-2-hydroxy-3-[N-(2-pyridyl)-methoxy-L-valyl] amino-4-phenylbutyl]-2,3-diaza-bicyclo-[2.2.1]heptane. This material (0.06 g; 0.113 mmol) and an equimolar amount of methyl L-2-isocyanato-3-methyl-butanoate were dissolved in 0.4 ml of ethanol free chloroform and to it was added 0.031 ml of diisopropylethylamine. The resulting mixture was allowed to stay for 12 hours at room temperature, under nitrogen, then diluted to 15 ml with ethyl acetate and washed with water and dried over magnesium sulfate. Evaporation in vacuo and purification by column chromatography (silica gel, ethyl acetate) gave 0.051 g (66%) of the title compound; melting point=79–84° C., $R_f$(C)=0.2; $R_f$(D)=0.46; NMR($CDCl_3$); 0.5–1.0 (m, 12H, val $CH_3$); 1.0–2.5 (m, 10H, val CH-β, butyl $CH_2$-1, $CH_2$-5,6,7); 2.5–3.33 (m, 3H, butyl $CH_2$-4, CH-3); 3.33–4.05 (m, 6H, val CH-α, CH-4, $OCH_3$); 4.05–5.5 (m, 6H, butyl CH-3, OH, CH-1, NH, methoxy $CH_2$); 5.82–6.7 (m, 2H, val NH); 6.9–7.9, 8.6 (m, m, 8H, 1H, aromatic).

EXAMPLE 18

2-t-Butoxycarbonyl-3-[(2RS, 3S)-2-hydroxy-3-(N-quinaldyl-L-asparaginyl)-amino-4-phenylbutyl]-1,2, 3,4-tetrahydrophthalazine Step A: 2-t-Butoxycarbonyl-3-[(2RS, 3S)-2-hydroxy-3-(phenylmethoxycarbonyl)amino-4-phenylbutyl]-1,2,3,4-tetrahydrophtalazine:

To a mixture of 0.19 g (1.11 mmol) of hydrochloride salt of 1,2,3,4-tetrahydrophthalazine [Groszkowski and Wesolowska, *Arch. Pharm.* (*Weinheim*) 314, 880 (1981)] and 0.23 g (1.05 mmol) of di-tert-butyl dicarbonate in 5 ml of chloroform was added 0.147 ml (1.05 mmol) of triethylamine under nitrogen. After stirring for 5 hours at room temperature the mixture was diluted to 30 ml with ethyl acetate, washed with water and saturated aqueous sodium chloride solution and dried over magnesium sulfate. Evaporation of the solvent in vacuo and purification of the residue by chromatography on silica gel (hexane/ethyl acetate 4:1) gave 0.0921 g (37%) of 2-t-butoxycarbonyl-1,2,3, 4tetrahydrophthalazine; NMR ($CDCl_3$) 1.5 (s, 9H, t-butoxy $CH_3$); 4.0 (s, 2H, $CH_2$-4); 4.47 (broad s, 1H, NH); 4.64 (s, 2H, $CH_2$-1); 6.95 (m, 4H, aromatic). When this material was substituted for 2-t-butoxy-carbonyl-2,3-diazabicyclo[2.2.1]-hept-5-ene in Step B of Example 14 a similar process afforded the title compound in 24% yield after purification on column chromatography (alumina, chloroform/ethyl acetate 95:5); melting point=68–71° C.; NMR ($CDCl_3$) 1.5 (s, 9H, t-butoxy $CH_3$); 2.18–3.15 (m, 4H, butyl $CH_2$-1,4); 3.3–5.5 (m, 10H, butyl CH-2,3, $CH_2$-1,4, methoxy $CH_2$, OH, NH); 7.22 (m, 14H, aromatic).

Step B: 2-t-Butoxycarbonyl-3-[(2RS, 3S)-2-hydroxy-3-(N-quinaldyl-L-asparaginyl)amino-4-phenylbutyl]- 1,2,3,4-tetrahydrophthalazine:

When the product of Step A is substituted for cis-1,6–3-t-Butoxycarbonyl-4-[(2RS,3S)-2-hydroxy-3-(phenylmethoxycarbonyl)amino-4-phenylbutyl]-3,4diazabicyclo[4.4.0]decane in Example 10 the identical process afforded the title compound in 70% yield; melting point= 108–112° C.; $R_f$(C)=0.44; $R_f$(D)=0.39; NMR ($CDCl_3$) 1.47 (m, 9H, t-butyl $CH_3$); 2.3–3.11 (m, 6H, asn $CH_2$, butyl $CH_2$-1,4); 3.2–5.14 (m, 8H, butyl CH-2,3, asn CH-α, $CH_2$-1,4, OH); 5.14–6.1 (m, 2H, NH); 6.6–7.4 (m, 10H, aromatic, NH); 7.62, 7.77, 7.87 (3×m, 1H, 1H, 1H, aromatic); 8.1–8.4 (m, 3H, aromatic); 9.11 (m, 1H, asn NH).

EXAMPLE 19 t-Butyl 3-isopropyl-3-[(2S, 3S)-2-hydroxy-3-(phenylmethoxycarbonyl)-amino-4-phenylbutyl] carbazate Step A: 2(R)-3(S)-1,2-Epoxy-3-phenylmethoxycarbonylamino4-phenylbutane:

To a stirred solution of 6.02 g (40 mmol) of sodium iodide in 50 ml of anhydrous acetonitrile was added 2.6 ml (22 mmol) of chlorotrimethylsilane under nitrogen. After 10 minutes of stirring, 6 g (20.1 mmol) of the predominantly erythro isomer of 2(R,S)-3(S)-1,2-Epoxy -3-phenylmethoxy-carbonylamino-4-phenylbutane (Example 6, Step A) was added and stirring was continued for additional 1 hour. To this mixture was added 4 g (61.2 mmol) of zinc dust followed by 6 ml of acetic acid. The resulting mixture was vigorously stirred for about 5 hours at room temperature and the solid material was removed by filtration. The filtrate was evaporated to dryness in vacuo and the residue was diluted to 75 ml with ether, washed with water and 5N aqueous sodium thiosulfate and dried over anhydrous magnesium sulfate. Evaporation in vacuo and purification by chromatography on silica gel (hexane/ethyl acetate 4:1) gave 5.1 g (90%) of (S)-2-(phenylmethoxy-carbonyl)amino-1-phenylbut-3-ene; $R_f$(A)=0.5; melting point=87–88° C. (hexane); NMR ($CDCl_3$) 2.87 (d, 2H, butene $CH_2$-1); 4.77 (m, 2H, butene $CH_2$-4); 5.0 (m, 1H, NCH); 5.06 (s, 2H, methoxy $CH_2$); 5.18 (broad d, 1H, NH); 5.55–6 (m, 1H, butene CH-3); 7.19, 7.27 (m, s, 5H, 5H, aromatic). This material (2.23 g; 7.93 mmol) was dissolved in 25 ml of dry methylene chloride and 4.5 g (22.1 mmol) of 85% 3-chloroperoxybenzoic acid was added at +4° C. The resulting mixture was stirred for two days at the above temperature, then diluted to 50 ml with ether, washed sequentially with 0° C. 10% aqueous sodium sulfite solution, saturated aqueous sodium bicarbonate and saturated aqueous sodium chloride and dried over magnesium sulfate. After evaporation of the solvent the crude product was purified by crystallization from a mixture of hexanelmethylene chloride to give 2.1 g (89% yield) of the title epoxide with the predominant threo stereochemistry; melting point= 83–84° C.; NMR ($CDCl_3$) 2.47 (m, 5H, butane CH2-1,4, CH-2); 3.74 (m, 0.15H, NCH); 4.2 (m, 0.85H, NCH); 4.53 (broad d, 1H, NH); 5.03 (m, 2H, methoxy $CH_2$); 7.3 (m, 10H, aromatic).

Step B: t-Butyl 3-isopropyl-3-[(2S, 3S)-2-hydroxy-3-(phenylmethoxycarbonyl)-amino-4-phenylbutyl]carbazate:

A mixture of 2.03 g (6.83 mmol) of the product of Step A and 1.2 g (7.6 mmol) of t-butyl 3-isopropylcarbazate in 8 ml of isopropanol was stirred for 12 hours at 70±5° C. under nitrogen. After evaporation of the solvent in vacuo the solid residue was recrystallised from hexane to give 2.6 g (80% yield) of the title compound melting at 114–115° C.; $R_f$(A)= 0.2; $R_f$(B)=0.61; NMR ($CDCl_3$) 0.95 (m, 6H, isopropyl CH$_3$); 1.42 (s, 9H, t-butyl CH$_3$); 2.44 (m, 2H, butyl CH$_2$-1); 2.94 (m, 3H, butyl CH$_2$-4, CH-3); 3.33–3.93 (m, 2H, isopropyl CH, butyl CH-2); 4.4 (broad m, 1H, OH); 5.05 (s, 2H, methoxy CH$_2$); 5.33 (broad m, 2H, NH); 7.18, 7.27 (m, s, 5H, 5H, aromatic).

EXAMPLE 20 t-Butyl 3-isopropyl-3-[(2S, 3S)-2-hydroxy-3-(N-quinaldyl-L-asparaginyl)-amino-4-phenylbutyl] carbazate When the product of Example 19 was substituted for t-butyl 3-isopropyl-[(2R, 3S)-2-hydroxy-3-(phenylmethoxycarbonyl)amino-4-phenylbutyl]carbazate in Example 3, the identical process afforded the title compound in 66% yield; melting point=203–204° C. (chloroform); R$_f$(C)=0.36; R$_f$(D)=0.37; NMR (5% CD$_3$OD in CDCl$_3$); 1.0 (m, 6H, isopropyl CH$_3$); 1.4 (s, 9H, t-butyl CH$_3$); 2.53 (d, 2H, butyl CH$_2$-1); 2.87 (m, 4H, asn CH$_2$, butyl CH$_2$-4); 3.13 (s, 6H, CD$_3$OH); 3.42 (m, 2H, isopropyl CH, butyl CH-3); 4.0 (m, 1H, butyl CH-2); 4.89 (m, 1H, asn CH-α); 7.11 (m, 5H, phenyl); 7.41–8.47 (m, 6H, quinaldyl).

EXAMPLE 21 cis-1,6-3-t-Butoxycarbonyl-4-[2S, 3S)-2-hydroxy-3-(phenylmethoxycarbonyl)-amino-4-phenylbutyl]-3,4-diaza-bicyclo[4.4.0]decane When the product of Step A, Example 8, is substituted for t-butyl 3-isopropyl-carbazate in Example 19, Step B, the identical process afforded the titled compound in 78%; melting point=110–111° C. (hexane); R$_f$(A)=0.28; R$_f$(B)=0.63; NMR (CDCl$_3$) 1.0–2.18 (m, 19H, decane CH$_2$-7,8,9,10, CH-1,6, t-butoxy CH$_3$); 2.4 (m, 2H, decane CH$_2$-5); 2.75–4.1 (m, 8H, decane CH$_2$-2, butyl CH2-1,4, CH-2,3); 4.93 (broad s, 1H, OH); 5.07 (s, 2H, methoxy CH$_2$); 5.31 (broad m, 1H, NH); 7.22, 7.32 (m, s, 5H, 5H, aromatic).

EXAMPLE 22 cis- 1,6-3-t-Butoxycarbonyl-4-[(2S, 3S)-2-hydroxy-3-amino-4-phenylbutyl]-3,4-diaza-bicyclo[4.4.0] decane According to the method of Example 2, step B, the product of Example 21 (2 g; 0.037 mol) was converted quantitatively to the title compound (1.5 g of a heavy syrup); NMR (CDCl$_3$) :1.0 –2.32 (m, 19H, decane CH$_2$-7,8,9,10, CH-1,6, t-butoxy CH$_3$); 2.32–4.54 (m, 13H, butyl CH$_2$-1,4, CH-2,3, decane CH$_2$-2,5, NH$_2$, OH); 7.28 (m, 5H, aromatic).

A fractional crystallisation of the above product from hexane gave 0.74 g of isomer A as a colorless solid melting at 123–124° C.; NMR (CDCl$_3$) 1.0–2.25 (m, 21H, decane CH$_2$-7,8,9,10, CH-1,6, t-butoxy CH$_3$, NH$_2$); 2.35–3.0 (m, 5H, butyl CH$_2$-1,4, CH-3); 3.05–3.4 (m, 3H, butyl CH-2, decane CH$_2$-5); 3.5 (m, 2H, decane CH$_2$-2); 3.82 (d, 1H, OH); 7.27 (m, 5H, aromatic).

The hexane fraction gave 0.76 g of isomer B, after evaporation of the solvent. This was purified by column chromatography (silica gel, 8% methanol in methylene chloride; Rf=0.16) to give 0.72 g of pure isomer B as a colorless syrup: NMR (CDCl$_3$) 1.0–2.4 (m, 21H, decane CH$_2$-7,8,9,10, CH-1,6, t-butoxy CH$_3$, NH$_2$); 2.4–3.1 (m, 6H, butyl CH$_2$-1,4, CH-2,3); 3.22–3.4 (m, 2H, decane CH$_2$-5); 3.52 (m, 2H, decane CH$_2$-2); 3.76 (d, 1H, OH); 7.27 (m, 5H, aromatic).

EXAMPLE 23 cis-1,6-3-t-Butoxycarbonyl-4-[(2S, 3S)-2-hydroxy-3-(N-quinaldyl-L-asparaginyl)amino-4-phenylbutyl]-3,4-diaza-bicyclo[4.4.0]decane When the product of Example 22 (mixture of isomers A and B) was substituted for cis-1,6-3-t-butoxycarbonyl-4-[(2RS,3S)-2-hydroxy-3-amino-4-phenylbutyl]-3,4-diaza-bicyclo[4.4.0]decane in Example 10, the identical process afforded the title compound in 72% yield; melting point= 108–25 110° C., Rf (C)=0.44; Rf (D)=0.46; NMR (CDCl$_3$) 0.71–2.18 (m, 19H, decane CH$_2$-7,8,9,10, CH-1,6, t-butoxy CH$_3$); 2.18–4.48 (m, 12H, asn CH$_2$, decane CH$_2$-2,5, butyl CH$_2$-1,4, CH-2,3); 4.95 (m, 2H, asn CH, OH); 5.55, 6.13 (broad m,m, 2H, NH); 6.84–7.4 (m, 6H, aromatic, NH); 7.4–8.39 (m, 6H, aromatic); 9.22 (m, 1H, NH).

A sample of this product was separated to two isomers by reverse phase (Whatman C$_8$ semipreparative column) high pressure liquid chromatography, using 37% of 0.1% aqueous solution of trifluoroacetic acid in acetonitrile containing 0.07% of trifluoroacetic acid and 10% of water, for the elution: Isomer A,Rf=16.8 min.; Isomer B,Rf=18.3 min.

When the isomers A and B of the product of Example 22 were used instead of mixture, the respective isomers of the title compound were obtained.

Isomer A: 69% yield; melting point=110–116° C.; NMR (CDCl$_3$): 1.0– 1.8 (m, 19H, t-butyl CH$_3$, decane CH$_2$-7,8, 9,10, CH-1,6); 2.2–2.6 (m, 2H, butyl CH$_2$-1); 2.7–3.3 (m, 7H, asn CH$_2$, butyl CH$_2$-4, CH-3, decane CH$_2$-5); 3.56 (m, 2H, decane CH$_2$-2); 4.07 (m, 1H, butyl CH-2); 5.0 (m, 1H, asn CH); 5.4–5.75 (m, 2H, NH, OH); 6.1 (m, 1H, NH); 7.14 (m, 6H, aromatic, NH); 7.63, 7.8, 8.22 (m, m, m, 1H, 2H, 3H, aromatic); 9.21 (m, 1H, asn NH).

Isomer B: 78% yield; melting pont=122–126° C.; NMR (CDCl$_3$): 1.1–1.71 (m, 19H, t-butyl CH$_3$, decane CH$_2$-7,8, 9,10, CH-1,6); 2.2–2.6 (m, 2H, butyl CH$_2$-1); 2.7–3.15 (m, 6H, asn CH$_2$, butyl CH$_2$-4 decane CH$_2$-5); 3.43 (m, 3H, butyl CH-3, decane CH$_2$-2); 4.1 (m, 1H, butyl CH-2); 4.94 (m, 1H, OH); 5.0 (m, 1H, asn CH); 5.55, 6.2 (m, m, 1H, 1H, NH$_2$); 7.14 (m, 6H, aromatic, NH); 7.63, 7.8, 8.22 (m, m, m, 1H, 2H, 3H, aromatic); 9.27 (m, $_1$H, asn NH).

EXAMPLE 24

1-Trimethylacetyl-2-[(2S,3S)-2-hydroxy-3-(phenylmethoxycarbonyl)amino-4-phenylbutyl]-2-isopropylhydrazine Step A: 1-trimethylacetyl-2-isopropylhydrazine:

A mixture of 10 g (0.086 mol) of methyl trimethylacetate and 3.2 g (0.1 mol) of anhydrous hydrazine was refluxed for 12 hr. then evaporated to dryness under reduced pressure. The residue was purified by crystallization from an ether/hexane mixture to give 9 g (90% yield) of trimethylacetylhydrazide, melting at 19014 191° C. When this product is substituted for t-butyl carbazate in Step A of Example 1 the identical process afforded the title compound in 67% yield, as colorless crystals; NMR (CDCl$_3$) 1.03 (d, 6H, isopropyl CH$_3$), 1.18 (s, 9H, trimethyl CH$_3$); 3.07 (m, 1H, isopropyl CH); 4,62 (broad s, 1H, NH); 7.4 (broad s, 1H, NH amide).

Step B: 1-trimethylacetyl-2-[(2S,3S)-2-hydroxy-3-(phenylmethoxycarbonyl)amino-4-phenylbutyl]-2-isopropyl-hydrazine:

When the product of Step A was substituted for t-butyl 3-isopropylcarbazate in Step B of Example 19, the identical process afforded the title compound in 69% yield; melting point=132–134° C.: Rf (A)=0.07; Rf (B)=0.33; NMR (CDCl₃) 0.72–1.3 (m, 15H, isopropyl CH₃, t-butyl CH₃); 2.1–3.16 (m, 5H, butyl CH₂-1,4, CH-3); 3.16–4.0 (m, 2H, butyl CH-2, isopropyl CH); 4.86 (s, 1H, OH); 5.08 (s, 2H, methoxy CH₂); 5.4 (d, 1H, NH); 6.1 (s, 1H, NH); 7.2, 7.31 (m, s, 5H, 5H aromatic).

EXAMPLE 25

1-Trimethylacetyl-2-[(2S,3S)-2-hydroxy-3-(N-quinaldyl-L-asparaginyl)amino-4-phenylbutyl]-2-isopropylhdyrazine When the product of Example 24 was substituted for t-butyl-3-isopropyl-[(2R,3S)-2-hydroxy-3-(phenylmethoxycarbonyl)amino-4-phenylbutyl]carbazate in Example 3, the identical process afforded the title compound in 65% yield; melting point=222–223.5° C.; Rf (C) =0.1; Rf (D)=0.49; NMR (10% CD₃OD in CDCl₃): 0.7–1.31 (m, 15H, trimethyl CH₃, isopropyl CH₃); 2.0–3.6 (m, 9H, asn CH₂, butyl CH₂-1,4, CH-2,3, isopropyl CH); 4.05 (s, CD₃OH), 5.0 (m, H, asn CH); 6.64–8.5 (m, 11H, aromatic).

EXAMPLE 26

1-(t-Butylamino)carbonyl-2-[(2S,3S)-2-hydroxy-3-(N-quinaldyl-L-asparaginyl)amino-4-phenylbutyl]-2-isopropylhydrazine To a vigorously stirred mixture of 0.33 g (0.0103 mol) of anhydrous hydrazine in 50 ml of dry ether was added 1 g (0.01 mol) of t-butyl isocyanate. The resulting mixture was stirred for 2 hr. at room temperature then was kept overnight at 4° C. The crystals formed were filtered off, washed with a small portion of ether and dried to give 0.94 g (72% yield) of (t-butylamino)carbonylhydrazine melting at 192–193° C. When this was substituted for t-butyl carbazate in Step A of Example 1, the identical process afforded 1-(t-butylamino) carbonyl-2-isopropylhydrazine in 58% yield as a white solid; NMR (CDCl₃): 1.03 (d, 6H, isopropyl CH₃); 1.33 (s, 9H, t-butyl CH₃); 3.9 (broad s. 1H, NH); 6.02 (broad s, 2H, NH amide). When this was substituted for t-butyl 3-isopropylcarbazate in Step B of Example 19 the identical process afforded 1-(t-butylamino)carbonyl-2-[(2S,3S)-2-hydroxy-3-(phenylmethoxycarbonyl)amino-4-phenylbutyl]-2-isopropylhydrazine in 68% yield, as a white solid; NMR (CDCl₃): 1.0 (m, 6H, isopropyl CH₃); 1.3 (s, 9H, t-butyl CH₃); 2.33–4.22 (m, BH, butyl CH₂-1,4, CH-2,3, OH, isopropyl CH); 5.05 (s, 2H, methoxy CH2); 5.3 (m, 2H, NH); 5.91(m 1H, NH); 7.2, 7.35 (m, s, 5H, 5H, aromatic). When this was substituted for t-butyl 3-isopropyl-[(2R, 3S)-2-hydroxy-3-(phenylmethoxycarbonyl)amino-4-phenylbutyl]carbazate in Example 3, the identical process afforded the title compound in 67% yield; melting point= 119–125° C.; Rf (C)=0.06; Rf (D)=0.43; NMR(CDCl₃): 1.0 (m, 6H, isopropyl CH₃); 1.32 (s, 9H, t-butyl CH₃); 2.24–3.38 (m, 7H, butyl CH₂-1,4, CH-3, asn CH₂); 3.38–4.63 (m, 3H, butyl CH-2, OH, isopropyl CH); 5.09 (m, 1H, asn CH); 5.63–8.4 (m, 16H, aromatic, NH); 9.0 (d, 1H, asn NH).

EXAMPLE 27 t-Butyl 3-isopropyl-3-[(2S, 3S)-2-hydroxy-3-(N-picolinyl-L-asparaginyl)amino-4-phenylbutyl] carbazate Stepf A: N-picolinyl-L-asparagine:

When picolinic acid was substituted s for quinaldic acid in Step A of Example 3, the identical process afforded the title compound melting at 171–172° C., in 68% yield, NMR(DMSO-d₆) 2.75 (m, 2H, asn CH₂); 4.8 (m, 1H, asn CH); 6.7–8.8 (m, 6H, aromatic, NH₂); 9.0 (d, 1H, NH); 12.7 (broad s, 1H, OH).

Step B: t-Butyl 3-isopropyl-3-[2S,3S)-2-hydroxy-3-(N-picolinyl-L-asparaginyl)amino-4-phenylbutyl]carbazate;

When the product of Step A was substituted for N-quinaldyl-L-aspargine in Example 20, the identical process afforded the title compound in 58% yield; melting point=101–108° C.; Rf (C)=0.16; Rf (D)=0.48; NMR (CDCl₃): 1.0 (m, 6H, isopropyl CH₃); 1.4 (s, 9H, t-butyl CH₃); 2.15–3.23(m 7H, butyl CH₂-1,4, CH-3, asn CH₂; 3.23–4.53 (m, 3H, butyl CH-2, isopropyl CH, OH); 4.94 (m, 1H, asn CH); 5.1–6.41 (m, 3H, NH); 6.7–8.7 (m, 1OH, aromatic, NH); 9.05 (m, 1H, asn NH).

EXAMPLE 28 t-Butyl 3-isopropyl-3-[(2S,3S)-2-hydroxy-3-(N-(2-pyridyl)methoxycarbonyl-anthranilyl)amino-4-phenylbutyl]carbazate When the product of Step A of Example 4 was substituted for N-quinaldyl-L-asparagine in Example 20, the identical process afforded the title compound in 61% yield; melting point=155–157° C.; Rf (C)=0.79; Rf (D)=0.78; NMR (CDCl₃): 1.0 (m, 6H, isopropyl CH₃); 1.42 (s, 9H, t-butyl CH₃); 2.33–3.22 (m, 5H, butyl CH₂-1,4 CH-2); 3.62 (m, 1H, butyl CH-3); 4.25 (m, 1H, isopropyl CH); 4.67 (broad s, 1H, OH); 5.3 (s, 2H, methoxy CH₂); 6.52–8.44 (m, 15H, aromatic, NH); 8.55 (m, 1H, NH).

EXAMPLE 29 t-Butyl 3-benzyl-3-[(2S,3S)-2-hydroxy-3-(phenylmethoxycarbonyl)amino-4-phenylbutyl] carbazate Step A: t-Butyl 3-benzylcarbazate:

When benzaldehyde was substituted for acetone in Step A of Example 1, the identical process afforded the title compound in 69% yield as a heavy colorless syrup; NMR (CDCl₃): 1.44 (s, 9H, t-butyl CH₃); 3.63 (broad s, 1H, NH); 4.0 (s, 2H, CH₂); 6.08 (s, 1H, NH); 7.3 (s, 5H, aromatic).

Step B: t-Butyl 3-benzyl-3-[(2S,3S)-2-hydroxy-3-(phenylmethoxycarbonyl)amino-4-phenylbutyl]carbazate:

When the product of Step A was substituted for t-butyl 3-isopropyl carbazate in Step B of Example 19, the identical process afforded the title compound in 72% yield; melting point=142–143° C.; Rf (A)=0.16; Rf (B)=0.59; NMR (CDCl₃) 1.31 (s, 9H, t-butyl CH₃); 2.12–3.12 (m, 5H, butyl CH₂-1,4, CH-3); 3.35–4.11 (m, 3H, benzyl CH₂, butyl CH-2); 4.41 (broad s, 1H, OH); 5.05 (s, 2H, methoxy CH₂); 5.2 (m, 2H, NH); 7.22 (m, 15H, aromatic).

EXAMPLE 30 t-Butyl 3-benzyl-3-[(2S,3S)-2-hydroxy-3-(N-quinaldyl-L-asparaginyl)amino-4-phenylbutyl] carbazate When the product of Example 29 was substituted for t-butyl 3-ispropyl-[(2S, 3S)-2-hydroxy-3-

(phenylmethoxycarbonyl)amino-4-phenylbutyl]carbazate in Example 20, the identical process afforded the title compound in 71% yield; melting point=150–153° C.; Rf (C)= 0.38; Rf (D)=0.53; NMR (CDCl$_3$): 1.3 (s, 9H, t-butyl CH$_3$); 2.13–3.2 (m, 7H, butyl CH$_2$-1,4, CH-3, asn CH$_2$); 3.2–4.73 (m, 4H, benzyl CH$_2$, butyl CH-2, OH); 5.0 (m, 1H, asn CH); 5.14–6.7 (m, 4H, NH); 6.7–8.35 (m, 16H aromatic); 9.25 (broad m, 1H, asn NH).

EXAMPLE 31 t-Butyl 3-cyclohexyl-3-[(2S, 3S)-2-hydroxy-3-(phenylmethoxycarbonyl)amino-4-phenylbutyl] carbazate Step A: t-Butyl 3-cyclohexylcarbazate:

When cyclohexanone was substituted for acetone in Step 1 of Example 1, the identical process afforded the title compound in 59% yield as a colorless solid; NMR (CDCl$_3$): 0.75–2.2 (m, 19H, t-butyl CH$_3$, cyclohexyl CH$_2$); 2.75 (m, 1H, cyclohexyl CH); 3.75 (broad s, 1H, NH); 6.27 (broad s, 1H, NH).

Step B: t-Butyl 3-cyclohexyl-3-[(2S,3S)-2-hydroxy-3-(phenylmethoxycarbonyl)amino-4-phenylbutyl]carbazate:

When the product of Step A was subsituted for t-butyl 3-isopropyl carbazate in Step B of Example 18, the identical process afforded the title compound in 76% yield; melting point=142–143° C.; Rf (A)=0.28; Rf (B)=0.7; NMR (CDCl$_3$): 0.73–2.0 (m, 19H, t-butyl CH$_3$, cyclohexyl CH$_2$); 2.53 (m, 3H, butyl CH$_2$-1, CH-3); 3.0 (d, 2H, butyl CH$_2$-4); 3.35–4.0 (m, 2H, butyl CH-2, cyclohexyl CH); 4.49 (broad s, 1H, OH); 5.13 (s, 2H, methoxy CH$_2$); 5.35 (m, 2H, NH); 7.3, 7.4 (m, s, 5H, 5H, aromatic).

EXAMPLE 32 t-Butyl 3-cyclohexyl-3-[(2S,3S)-2-hydroxy-3-(N-quinaldyl-L-asparaginyl)amino-4-phenylbutyl] carbazate When the product of Example 31 was substituted for t-butyl 3-isopropyl-3-[(2S, 35)-2-hydroxy-3-(phenylmethoxycarbonyl)amino-4-phenylbutyl]-carbazate in Example 20, the identical process afforded the title compound in 75% yield: melting point=140–144° C;. Rf (C)0.42; Rf (D)=0.56; NMR (CDCl$_3$): 0.7–2.17 (m, 19H, t-butyl CH$_3$, cyclohexyl CH$_2$); 2.17–3.29 (m, 7H, butyl CH$_2$-1,4, CH-3 asn CH$_2$); 3.3–4.87 (m, 3H, butyl CH-2, cyclohexyl CH, OH): 4.95 (m, 1H, asn CH); 5.14–6.4 (m, 3H, NH); 6.62–8.3 (m, 12H, aromatic, NH); 9.15(d, 1H, asn NH).

EXAMPLE 33 t-Butyl 3-isopropyl-3-[(2S,3S)-2-hydroxy-3-(N-(1-carbamoylmethyl)acrylyl)-amino-4-phenylbutyl] carbazate Step A: (1-Carbamoylmethyl)acrylic acid:

To a mixture of 3 g (0.027 mol) of itaconic anhydride in 30 ml of tetrahydrofuran, 3 ml of 28% ammonium hydroxide was added. After 1 hr. the reaction mixture was evaporated to dryness under reduced pressure. The residue was dissolved in 15 ml of water, then acidified to pH 2 with concentrated hydrochloric acid and allowed to stay overnight at 40. The precipitate formed was filtered off, washed with a small portion of cold water and dried to give 1.4 g (40% yield) of the title compound melting at 153–154° C.; NMR (DMSO-d$_6$): 3.11 (s, 2H, CH$_2$); 5.67,6.13 (s, s, 1H, 1H, CH); 6.7, 7.9 (broad s, s 1H, 1H, NH); 12.15 (broad s, 1H, OH).

Step B: t-Butyl 3-isopropyl-3-[(2S,3S)-2-hydroxy-3-(N-(1-carbamoyl-methyl)acryloyl)amino-4-phenylbutyl] carbazate:

When the product of Step A was substituted for N-quinaldyl-L-asparagine in Example 20, the identical process afforded the title compound in 61% yield; melting point=118–122° C.; Rf (C)=0.27; Rf (D)=0.49; NMR (CDCl$_3$): 1.0 (m, 6H, isopropyl CH$_3$); 1.4 (s, 9H, t-butyl CH$_3$); 2.49 (m, 2H, butyl CH$_2$-1); 3.0 (m, 3H, butyl CH$_2$-4, CH-3); 3.2 (s, 2H, methyl CH$_2$); 3.6 (m, 1H, isopropyl CH); 4.07 (m, 1H, butyl CH-2); 4.6 (broad s, 1H, OH); 5.2–5.8 (m, 4H, acryl CH, NH); 6.4–7.0 (m, 2H, NH$_2$); 7.2 (m, 5H, aromatic).

EXAMPLE 34 t-Butyl 3-isopropyl-3-[(2S,3S)-2-hydroxy-3-(N-2-(RS)-3-tert-butylthio-2-carbamoylmethylpropionyl) amino-4-phenylbutyl]carbazate To a mixture of 0.057 g (0.127 mmol) of the product of Example 33 and 0.0172 ml (0.152 mmol) of tert-butyl mercaptan in 0.5 ml of anhydrous methanol, 1 drop of a freshly prepared 20% solution of sodium methoxide in methanol was added. After stirring for 12 hr. at room temperature the mixture was evaporated to dryness, then diluted to 10 ml with ether and washed with water and saturated sodium chloride solution. After drying over anhydrous magnesium sulfate, the ether was evaporated under reduced pressure. The residue was purified by column chromatography (silica gel; ethyl acetate), to give 0.032 g (47% yield) of the title compound; melting point=116–120° C.; Rf (C)=0.42; Rf (D)=0.56; NMR (CDCl$_3$): 0.6–1.63 (m, 24H, t-butyl CH$_3$, isopropyl CH$_3$); 2.0–4.47 (m, 13H, butyl CH$_2$-1,4, CH-2,3, isopropyl CH, methyl CH$_2$, propionyl CH$_2$, CH, OH); 4.82–6.78 (m, 4H, NH$_2$, NH); 7.11 (m, 5H, aromatic)

EXAMPLE 35 t-Butyl 3-isopropyl-3-[(2S, 3S)-2-hydroxy-3-(N-benzoyl-L-asparaginyl)amino-4-phenylbutyl] carbazate Step A: N-Benzoyl-L-asparagine:

To a vigorously stirred solution of 2 g (0.013 mol) of L-asparagine monohydrate and 2.02 g (0.014 mol) of potassium carbonate in 15 ml of water, 1.51 ml (0.013 mol) of benzoyl chloride was added dropwise, over a period of 15 min., at room temperature. The stirring was continued for 2 hour, then the mixture was extracted with 10 ml of ether and the aqueous phase was acidified to pH 2 with concentrated hydrochloric acid. The white precipitate was filtered off, washed with water and purified by crystallization from isopropyl alcohol to give 2.1 g (68% yield) of the title compound at 190–192° C.; NMR (DMSO-d$_6$): 2.62 (m, 2H, CH$_2$); 3.32 (broad s, 1H, OH); 4.72 (m, 1H, CH); 6.64–8.0 (m. 7H, aromatic, NH$_2$); 8.6 (d, 1H, NH).

Step B: t-Butyl 3-isopropyl-3-[(2S,3S)-2-hydroxy-3-(N-benzoyl-L-asparaginyl)-amino-4-phenylbutyl]carbazate:

When the product of Step A was substituted for N-quinaldyl-L-asparagine in Example 20, the identical process afforded the title compound in 65% yield; melting point=182–185° C.; Rf (C)=0.22; Rf (D) =0.51; NMR (CDCl$_3$/DMSO-d$_6$, 1:1): 0.92 (m, 6H, isopropyl CH$_3$); 1.38

(s, 9H, t-butyl CH₃); 2.19–3.11 (m, 7H, butyl CH₂-1,4, CH-3, asn CH₂); 3.11–4.57 (m, 3H, isopropyl CH, butyl CH-2, OH); 4.83 (m, 1H, asn CH); 6.5–8.17 (m, 14H, aromatic NH); 8.56 (m, 1H, asn NH).

EXAMPLE 36

1-t-Butyloxycarbonyl-2-[(2S,3S)-2-hydroxy-3-(phenylmethoxycarbonyl)amino-4-phenylbutyl]hexahydropyridazine Step A: 1-t-butyloxycarbonylhexahydropyridazine:

When 1,4-dibromobutane was substituted for cis-1,2-cyclohexanedimethyliodide in Step A of Example 8, the identical process afforded 1-t-butoxycarbonyl-2-phenylmethoxycarbonylhexahydropyridazine in 65% yield; melting point=71–72° C.; NMR (CDCl₃) 1.15–1.9 (m, 13H, t-butyl CH₃; CH₂-4,5); 3.0, 4.15 (broad m, m, 2H, 2H, CH₂-3,6); 5.2 (m, 2H, methoxy CH₂); 7.35 (s, 5H, aromatic). This was converted to the title compound in 93% yield by hydrogenolysis, performed as described in Example 2. The product was isolated as a colorless syrup.

Step B: 1-t-butyloxycarbonyl-2-[(2S,3S)-2-hydroxy-3-(phenylmethoxycarbonyl)amino-4-phenylbutyl]hexahydropyridazine:

When the product of Step A was substituted for t-butyl 3-isopropylcarbazate in Step B of Example 19 the identical process afforded the title compound in 71% yield, as a heavy colorless syrup; NMR (CDCl₃) 1.0–1.87 (m, 13H, t-butyl CH₃, pyridazine CH₂-4,5); 2.0–4.0 (m, 11H, butyl CH₂-1,4, CH-2,3, pyridazine CH₂-3,6, OH); 5.05 (s, 2H, methoxy CH₂); 5.47(d, 1H, NH); 7.19 (m, 1OH, aromatic).

EXAMPLE 37

1-t-Butyloxycarbonyl-2-[(2S, 3S)-2-hydroxy-3-(N-quinaldyl-L-asparaginyl)-amino-4-phenylbutyl]hexahydropyridazine When the product of Example 36 was substituted for t-butyl 3-isopropyl-[(2S,3S)-2-hydroxy-3-(phenylmethoxycarbonyl)amino-4-phenylbutyl]carbazate in Example 20, the identical process afforded the title compound in 65% yield; melting point=104–110° C.; Rf (C)= 0.3; Rf (D)=0.62; NMR (CDCl₃) 1.0–2.04 (m, 13H, t-butyl CH₃, pyridazine CH₂-4,5); 2.15–4.31 (m, 13H, butyl CH₂-1,4, CH-2,3, asn CH₂, pyridazine CH₂-3,6, OH); 4.95 (m, 1H, asn CH); 5.14–6.6 (m, 3H, NH); 6.8–8.4 (m, 11H, aromatic); 9.21(d, 1H, asn NH).

EXAMPLE 38 cis-1.6-3-t-Butoxycarbonyl-4-[(2S,3S)-2-hydroxy-3-(N-quinaldyl-3-cyano-L-alanyl)amino-4-phenylbutyl]-3,4-diaza-bicyclo[4.4.0]decane Step A: N-Quinaldoyl-3-cyano-L-alanine:

To a mixture of 0.198 g (0.69 mmol) of N-quinaldyl-L-asparagine and 0.24 ml (1.38 mmol) of N, N-diisopropylethylamine in 1 ml of chloroform was added 0.146 g (0.71 mmol) of dicyclohexylcarbodiimide. The reaction mixture was stirred for 24 hr. at room temperature, then partitioned between 10 ml of 5% sodium bicarbonate and 10 ml of ether. The aqueous phase was acidified to pH2 and the acid was taken up by extraction with chloroform (3× ml). The organic phase was dried over anhydrous magnesium sulfate, filtered and evaporated to give 0.101 g of crude product. This was recrystallized from a small portion of methylene chloride to give 0.06 g of the title compound melting at 144–146° C.; NMR (5% DMSO-d₆ in CDCl₃): 3.22 (d, 2H, ala CH₂); 4.95 (m, 1H, ala CH); 7.2–8.57 (m, 7H, aromatic, OH); 9.19(d, 1H, NH).

Step B: cis-1.6-3-t-Butoxycarbonyl-4-[(2S,3S)-2-hydroxy-3-(N-quinaldyl-3-cyano-L-alanyl)amino-4-phenylbutyl]-3,4-diaza-biyclo[4.4.0]decane:

When the product of Step A was substituted for N-quinaldyl-L-asparagine in Example 22 (isomer A) the identical process afforded the title compound with 67% yield, melting at 106–112° C.; Rf (C)=0.87; Rf (D)=0.89; NMR (CDCl₃) 0.7–2.84 (m, 24H, t-butyl CH₃, decane CH₂-7,8,9,10, CH-1,6, butyl CH₂-1, CH-3, cyanoalanyl CH₂); 2.85–4.65 (m, 8H, butyl CH₂-4, CH-2, decyl CH₂-2,5. OH); 4.7–5.6 (broad m, 2H, cyanoalanyl CH, NH); 6.9–8.5 (m, 11H, aromatic); 8.9 (broad m, 1H, NH).

I claim:

1. A compound of formula (I):

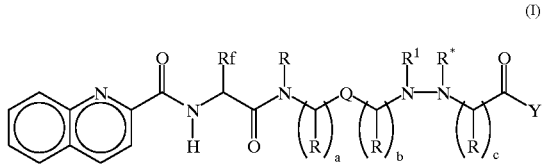

or pharmaceutically acceptable salts thereof, wherein:

$R_f$ is the side-chain of a natural amino acid in which any functional group present is optionally protected;

each R is independently selected from the group consisting of hydrogen, —R'H, —R'C(O)OR", —R'C(O)NH₂, —R'C(O)NHR", —R'C(O)NR"R'", —R'NHC(O)R" and —R'C(O)R", where R" and R'" are $(C_1–C_{12})$alkyl, $(C_3–C_{12})$cycloalkyl, $(C_3–C_{12})$cycloalkyl$(C_1–C_6)$alkyl, $(C_6–C_{12})$aryl, $(C_7–C_{16})$aralkyl, $(C_2–C_{12})$alkenyl, $(C_8–C_{16})$aralkenyl, $(C_2–C_{12})$alkynyl, $(C_8–C_{16})$aralkynyl or heterocyclic, and R' is an optionally substituted divalent radical derived from $(C_1–C_{12})$alkyl, $(C_3–C_{12})$cycloalkyl, $(C_3–C_{12})$cycloalkyl$(C_1–C_6)$alkyl, $(C_6–C_{12})$aryl, $(C_7–C_{16})$aralkyl, $(C_2–C_{12})$alkenyl, $(C_8–C_{16})$aralkenyl, $(C_2–C_{12})$alkynyl, $(C_8–C_{16})$-aralkynyl or heterocyclic; or wherein any two R substituents, not necessarily vicinal, taken together are optionally substituted linear $(C_2–C_8)$ alkylidene;

$R^1$, $R^*$ and the nitrogen atoms to which they are bound together form a cyclic diazaalkane selected from the group consisting of:

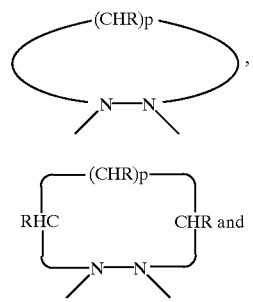

-continued wherein p is 1 to 3, each R is independently as defined above and $R^8$ is R, —$NH_2$, —NHR, —$NR_2$, —COOH, —COOL, —CHO, —C(O)R, —CN, halo, —$CF_3$, —OL, —SR, —S(O)R, —$S(O)_2R$, —$CONH_2$, —CONHR, —$CONR_2$, —NHOH, —NHOL, —$NO_2$, —O, —S or —$NHNH_2$, wherein each R is independently as defined above and each L is R or a protecting group that protects the hydroxyl group during synthesis and/or prevents premature metabolism of the compound of formula (I);

Y is hydrogen, —R or —OR, where R is as previously defined, or is an amino acid or peptide residue in which any functional group present is optionally protected;

a and b are independently 0 to 4 and c is 0 to 6; and Q is $$-CR- \quad -C-CR_2- \quad or \quad -CR-CR_2$$
$$\phantom{-CR-}OL \phantom{xx} \phantom{-C-}O \phantom{xxxx} \phantom{-CR-}OL$$

where L is as previously defined and each R, independently of the others, are as previously defined.

2. A compound according to claim 1 having the structure represented by formula (IC) or (ID):

(IC)

(ID)

wherein:
R is as defined in claim 1;
$R^{21}$ is hydrogen, optionally substituted ($C_1$–$C_{12}$)alkyl; optionally substituted ($C_6$–$C_{12}$)aryl; or optionally substituted ($C_7$–$C_{16}$) aralkyl; $R^{22}$ is hydrogen, ($C_1$–$C_8$) alkyl; or ($C_7$–$C_{16}$) aralkyl; or wherein R 21 and $R^{22}$ taken together are —$(CH_2)_n$—, wherein n is 2–8;
$NR^1$ and NR* taken together may be a cyclic diazalkane as defined in claim 1;
Y and $R_f$ are as defined in claim 1; and
L is R or a protecting group that protects the hydroxyl group during synthesis and/or prevents premature metabolism of the compound of formula (IC).

3. A compound according to claim 1, which is
(i) cis-1,6-3-t-butoxycarbonyl-4-[(2R or S,3S)-2-hydroxy-3-(N-quinaldyl-L-valyl)amino-4-phenylbutyl]-3,4-diazabicyclo[4.4.0]decane, (ii) cis-1,6-3-t-butoxycarbonyl-4-[(2R or S,3S)-2-hydroxy-3-(N-quinaldyl-L-asparaginyl)amino-4-phenylbutyl]-3,4-diazabicyclo[4.4.0]decane, (iii) cis-1,6-3-t-butoxycarbonyl-4-[(2R or S,3S)-2-hydroxy-3-(N-quinaldyl-L-glutaminyl)amino-4-phenylbutyl]-3,4-diazabicyclo[4.4.0]decane, (iv) cis-1,6-3-t-butoxycarbonyl-4-[(2R or S,3S)-2-hydroxy-3-(N-quinaldyl-L-threonyl)amino-4-phenylbutyl]-3,4-diazabicyclo[4.4.0]decane, (v) 2-t-butoxycarbonyl-3-[(2R or S,3S)-2-hydroxy-3-(N-quinaldyl-L-asparaginyl)amino-4-phenylbutyl]-2,3-diazabicyclo[2.2.1]heptane, (vi) 2-t-butoxycarbonyl-3-[(2R or S,3S)-2-hydroxy-3-(N-quinaldyl-L-asparaginyl)amino-4-phenylbutyl]-1,2,3,4-tetrahydrophthalazine or (vii) 1-t-butyloxycarbonyl-2[(2S,3S)-2-hydroxy-3-(N-quinaldyl-L-asparaginyl)amino-4-phenylbutyl] hexahydropyridazine.

4. A compound according to claim 1, said compound having the formula where L is H or a protecting group that protects the hydroxyl group during synthesis and/or prevents premature metabolism of the compound.

5. A compound according to claim 1 wherein Q is $$-CH-$$
$$\phantom{-}OL$$

a and b are both 1, and c=0.

6. A compound according to claim 1 wherein Q is $$-C-CH_2-$$
$$\|$$
$$O$$

a=1 and b and c are both 0.

7. A compound which is cis-1,6-3-t-butoxycarbonyl-4-[2S, 3S)-2-hydroxy-3-(N-quinaldyl-L-asparaginyl)amino-4-phenylbutyl]-3,4-diazabicyclo[4.4.0]decane.

8. A pharmaceutical composition comprising a compound according to claim 1 together with one or more pharmaceutically acceptable carriers.

9. A pharmaceutical composition comprising a compound according to claim 2 together with one or more pharmaceutically acceptable carriers.

10. A pharmaceutical composition comprising a compound according to claim 3 together with one or more pharmaceutically acceptable carriers.

11. A pharmaceutical composition comprising a compound according to claim 4 together with one or more pharmaceutically acceptable carriers.

12. A pharmaceutical composition comprising a compound according to claim 5 together with one or more pharmaceutically acceptable carriers.

13. A pharmaceutical composition comprising a compound according to claim 6 together with one or more pharmaceutically acceptable carriers.

14. A pharmaceutical composition comprising a compound according to claim 7 together with one or more pharmaceutically acceptable carriers.

15. A method for inhibiting an HIV protease in need of such protease inhibition, said method comprising administering to said mammal an effective amount of a pharmaceutical composition according to claim 8.

16. A method for inhibiting an HIV protease in need of such protease inhibition, said method comprising administering to said mammal an effective amount of a pharmaceutical composition according to claim 9.

17. A method for inhibiting an HIV protease in need of such protease inhibition, said method comprising administering to said mammal an effective amount of a pharmaceutical composition according to claim 10.

18. A method for inhibiting an HIV protease in need of such protease inhibition, said method comprising administering to said mammal an effective amount of a pharmaceutical composition according to claim 11.

19. A method for inhibiting an HIV protease in need of such protease inhibition, said method comprising administering to said mammal an effective amount of a pharmaceutical composition according to claim 12.

20. A method for inhibiting an HIV protease in need of such protease inhibition, said method comprising administering to said mammal an effective amount of a pharmaceutical composition according to claim 13.

21. A method for inhibiting an HIV protease in need of such protease inhibition, said method comprising administering to said mammal an effective amount of a pharmaceutical composition according to claim 14.

* * * * *